(12) United States Patent
Puetz et al.

(10) Patent No.: US 6,673,794 B2
(45) Date of Patent: Jan. 6, 2004

(54) SUBSTITUTED AMINOMETHYL-PHENYL-CYCLOHEXANE DERIVATIVES

(75) Inventors: Claudia Puetz, Dueren (DE); Wolfgang Strassburger, Wuerselen (DE); Babette-Yvonne Koegel, Langerwehe-Hamich (DE)

(73) Assignee: Gruenenthal GmbH, Aachen (DE)

( * ) Notice: Subject to any disclaimer, the term of this patent is extended or adjusted under 35 U.S.C. 154(b) by 0 days.

(21) Appl. No.: 10/189,190

(22) Filed: Jul. 5, 2002

(65) Prior Publication Data

US 2003/0069288 A1 Apr. 10, 2003

Related U.S. Application Data

(63) Continuation of application No. PCT/EP00/13281, filed on Dec. 27, 2000.

(30) Foreign Application Priority Data

Jan. 5, 2000 (DE) .......................................... 100 00 312

(51) Int. Cl.[7] .................... A61K 31/535; A61K 31/445; A61K 31/20; A01N 43/40; A01N 37/00
(52) U.S. Cl. .................... 514/239.5; 514/331; 514/539; 514/568; 514/620; 514/646; 544/106; 544/158; 544/162; 544/170; 546/192; 546/234; 546/236; 560/42; 562/451; 564/164; 564/165; 564/442; 564/443; 564/305
(58) Field of Search .......................... 560/42; 562/451; 564/164, 165, 442, 443, 305; 514/539, 568, 620, 659, 646, 331, 239.5; 544/106, 158, 162, 170; 546/192, 234, 236

(56) References Cited

U.S. PATENT DOCUMENTS 5,733,936 A * 3/1998 Buschmann et al. ........ 514/646
5,801,201 A * 9/1998 Graudums et al. .......... 514/646
6,323,369 B1   11/2001 Zimmer et al. ............. 564/337

FOREIGN PATENT DOCUMENTS

DE          19857475 A1   12/1998

OTHER PUBLICATIONS

Kato et al, "Synthesis and Analgesic Activity of Cyclohexenylmethylamines and Related Compounds" Chem. Pharm. Bull. vol. 32(6), pp. 2279–2289 (1984).*

Shipton, E. A. "Tramadol—Present and Future" Anesth. Intensive Care. vol. 28(4), pp. 363–3784 (Aug., 2000).*

Tramadol® Prescribing Information. Product package insert. Ortho–Mcneil Pharmaceutical, Inc. Raritan, NJ (2001).*

* cited by examiner

Primary Examiner—Richard L. Raymond
Assistant Examiner—Zachary C. Tucker
(74) Attorney, Agent, or Firm—Crowell & Moring LLP

(57) ABSTRACT

A substituted aminomethyl-phenyl-cyclohexane derivative of formula I or Ia,

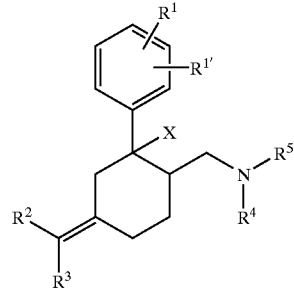

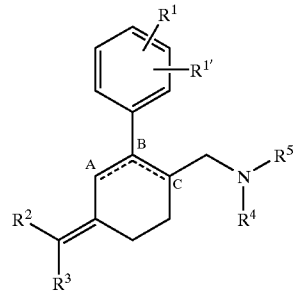

and their a diastereomer, enantiomer, or of a salt formed with a physiologically tolerated acid. Also disclosed are method for preparing the substituted aminomethyl-phenyl-cyclohexane derivative, pharmaceutical compositions comprising the same and method of using the same for treating pain, urinary incontinence, itching, diarrhea, inflammatory and allergic reactions, depression, drug or alcohol abuse, gastritis, cardiovascular diseases, respiratory tract diseases, coughing, mental illnesses and epilepsy.

61 Claims, No Drawings

SUBSTITUTED AMINOMETHYL-PHENYL-CYCLOHEXANE DERIVATIVES

CROSS REFERENCE TO RELATED APPLICATIONS

The present application is a continuation of international patent application no. PCT/EP00/13281, filed Dec. 27, 2000, designating the United States of America, the entire disclosure of which is incorporated herein by reference. Priority is claimed based on Federal Republic of Germany patent application no. 100 00 312.5, filed Jan. 5, 2000.

BACKGROUND AND SUMMARY OF THE INVENTION

The present invention relates to substituted aminomethyl-phenyl-cyclohexane derivatives and processes for their preparation, their use for the preparation of medicaments and medicaments comprising these compounds.

Treatment of chronic and non-chronic states of pain is of great importance in medicine. There is a worldwide need for pain treatments with a good action for target-orientated treatment of chronic and non-chronic states of pain appropriate for the patient, by which is to be understood successful and satisfactory pain treatment for the patient. This manifests itself in the large number of scientific works which have been published in the field of applied analgesia and basic research in nociception in recent years.

Conventional opioids, such as morphine, have a good action in the treatment of severe to very severe pain. However, their use is limited by their known side effects, e.g. respiratory depression, vomiting, sedation, constipation, addiction, dependency and development of tolerance. They can therefore be administered over a relatively long period of time or in relatively high dosages only if particular safety precautions are taken, such as specific prescription instructions (Goodman, Gilman, The Pharmacological Basis of Therapeutics, Pergamon Press, New York 1990). They furthermore show a lower activity with some states of pain, in particular neuropathic pain.

Tramadol hydrochloride—(1RS,2RS)-2-[(dimethylamino)methyl]-1-(3-methoxyphenyl) cyclohexanol hydrochloride—is another known therapeutic for treatment of severe pain. It occupies a special position among analgesics having an action on the central nervous system, inasmuch as this active compound brings about potent inhibition of pain without the side effects known of opioids (J. Pharmacol. Exptl. Ther. 267, 33 (1993)), both the enantiomers of tramadol and the enantiomers of tramadol metabolites participating in the analgesic action (J. Pharmacol. Exp. Ther. 260, 275 (1992)). Needless to say, tramadol is also not without side effects.

There is thus a need to provide substances which have an analgesic action and are suitable for treatment of pain. These substances should furthermore have as few side effects as possible, such as nausea, dependency, respiratory depression or constipation.

DETAILED DESCRIPTION OF THE INVENTION

This object is achieved by the substituted aminomethyl-phenyl-cyclohexane derivatives according to the invention. The invention therefore provides substituted aminomethyl-phenyl-cyclohexane derivatives of the general formula I and Ia, also in the form of their diastereomers or enantiomers and of their free bases or of a salt formed with a physiologically tolerated acid, in particular the hydrochloride salt.

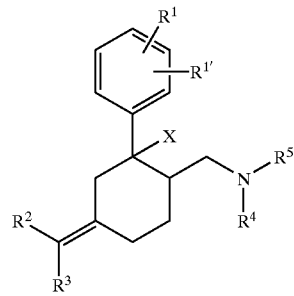

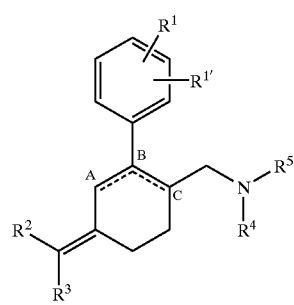

wherein
$R^1$ and $R^{1'}$ independently of one another are
H, $C_1$–$C_{10}$-alkyl, $C_2$–$C_{10}$-alkenyl or $C_2$–$C_{10}$-alkinyl, in each case branched or unbranched and mono- or polysubstituted or unsubstituted; F; Cl; Br; I; $NR^6R^{6'}$; $NO_2$; CN; $OR^6$; $SR^6$; $OC(O)R^6$; $C(O)OR^6$; $C(O)R^6$ or $C(O)NR^6R^6$, wherein $R^6$ and $R^{6'}$ are
H; $C_1$–$C_{10}$-alkyl, $C_2$–$C_{10}$-alkenyl or $C_2$–$C_{10}$-alkinyl, in each case branched or unbranched and mono- or polysubstituted or unsubstituted; $C_3$–$C_7$-cycloalkyl, saturated or unsaturated and mono- or polysubstituted or unsubstituted, or a corresponding heterocyclic radical, in which one C atom in the ring is replaced by N, S or O; alkylaryl, saturated or unsaturated and mono- or polysubstituted or unsubstituted; or aryl or heteroaryl, in each case mono- or polysubstituted or unsubstituted; or
$R^1$ and $R^1$ together form —CH=CH—CH=CH— resulting in a naphthyl system which can be mono- or polysubstituted,
X is
H, F, Cl, Br, I, $CF_3$, $OS(O_2)C_6H_4$-$pCH_3$, $OR^7$ or $OC(O)R^7$, wherein $R^7$ is
H; $C_1$–$C_{10}$-alkyl, $C_2$–$C_{10}$-alkenyl or $C_2$–$C_{10}$-alkinyl, in each case branched or unbranched and mono- or polysubstituted or unsubstituted; $C_3$–$C_7$-cycloalkyl, saturated or unsaturated and mono- or polysubstituted or unsubstituted, or a corresponding heterocyclic radical, in which one C atom in the ring is replaced by N, S or O; alkylaryl, saturated or unsaturated and mono- or polysubstituted or unsubstituted; or aryl or heteroaryl, in each case mono- or polysubstituted or unsubstituted; or
if the compound contains no X, according to formula Ia a double bond is formed between C atom A and C atom B or C atom B and C atom C,
$R^4$, $R^5$ independently of one another are
H; $C_1$–$C_{10}$-alkyl, $C_2$–$C_{10}$-alkenyl or $C_2$–$C_{10}$-alkinyl, in each case branched or unbranched and mono- or polysubstituted or unsubstituted; $C_3$–$C_7$-cycloalkyl, saturated or unsaturated and mono- or polysubstituted or unsubstituted, or a corresponding heterocyclic radical, in which one C atom in the ring is replaced by N, S or O; alkylaryl, saturated or unsaturated and mono- or polysubstituted or unsubstituted; or aryl or heteroaryl, in each case mono- or polysubstituted or unsubstituted; or $R^4$ and $R^5$ together form a $C_3$–$C_7$-cycloalkyl, saturated or unsaturated and mono- or polysubstituted or unsubstituted, or a corresponding heterocyclic radical, in which one C atom in the ring is replaced by S, O or $NR^8$, wherein $R^8$ is H; or $C_1$–$C_{10}$-alkyl, $C_2$–$C_{10}$-alkenyl or $C_2$–$C_{10}$-alkinyl, in each case branched or unbranched and mono- or polysubstituted or unsubstituted;

and $R^2$, $R^3$ independently of one another are $R^9$ or $YR^9$, wherein Y is $C_1$–$C_{10}$-alkyl, $C_2$–$C_{10}$-alkenyl or $C_2$–$C_{10}$-alkinyl, branched or unbranched and mono- or polysubstituted or unsubstituted, wherein $R^9$ is H; F; Cl; Br; I; CN; $NO_2$; $C_1$–$C_{18}$-alkyl, $C_2$–$C_{18}$-alkenyl or $C_2$–$C_{18}$-alkinyl, in each case branched or unbranched and mono- or polysubstituted or unsubstituted; or $C_3$–$C_7$-cycloalkyl, saturated or unsaturated and mono- or polysubstituted or unsubstituted, or a corresponding heterocyclic radical, in which one C atom in the ring is replaced by S, O or $NR^{10}$, where $R^{10}$ is H; or $C_1$–$C_{10}$-alkyl, $C_2$–$C_{10}$-alkenyl or $C_2$–$C_{10}$-alkinyl, in each case branched or unbranched and mono- or polysubstituted or unsubstituted;

$OR^{11}$, $OC(O)R^{11}$, $OC(O)OR^{11}$, $OC(S)R^{11}$, $C(O)R^{11}$, $C(O)OR^{11}$, $C(S)R^{11}$, $C(S)OR^{11}$, $SR^{11}$, $S(O)R^{11}$ or $S(O_2)R^{11}$, wherein $R^{11}$ is H; $C_1$–$C_{18}$-alkyl, $C_2$–$C_{18}$-alkenyl or $C_2$–$C_{18}$-alkinyl, in each case branched or unbranched and mono- or polysubstituted or unsubstituted; $C_3$–$C_7$-cycloalkyl, saturated or unsaturated and mono- or polysubstituted or unsubstituted, or a corresponding heterocyclic radical, in which one C atom in the ring is replaced by S, O or $NR^{12}$, where $R^{12}$ is chosen from H, $C_1$–$C_{10}$-alkyl, $C_2$–$C_{10}$-alkenyl or $C_2$–$C_{10}$-alkinyl, in each case branched or unbranched and mono- or polysubstituted or unsubstituted;

alkylaryl, saturated or unsaturated and mono- or polysubstituted or unsubstituted; or aryl or heteroaryl, in each case mono- or polysubstituted or unsubstituted;

$NR^{13}R^{14}$, $NR^{13}C(O)R^{14}$, $C(O)NR^{13}R^{14}$ or $S(O_2)NR^{13}R^{14}$, wherein $R^{13}$ and $R^{14}$ independently of one another are H; O; $C_1$–$C_{18}$-alkyl, $C_2$–$C_{18}$-alkenyl or $C_2$–$C_{18}$-alkinyl, in each case branched or unbranched and mono- or polysubstituted or unsubstituted; $C_3$–$C_7$-cycloalkyl, saturated or unsaturated and mono- or polysubstituted or unsubstituted, or a corresponding heterocyclic radical, in which one C atom in the ring is replaced by S, O or $NR^{15}$, where $R^{15}$ is H, $C_1$–$C_{10}$-alkyl, $C_2$–$C_{10}$-alkenyl or $C_2$–$C_{10}$-alkinyl, in each case branched or unbranched and mono- or polysubstituted or unsubstituted;

alkylaryl, saturated or unsaturated and mono- or polysubstituted or unsubstituted; or aryl or heteroaryl, in each case mono- or polysubstituted or unsubstituted; or $R^{13}$ and $R^{14}$ together form a $C_3$–$C_7$-cycloalkyl, saturated or unsaturated and mono- or polysubstituted or unsubstituted, or a corresponding heterocyclic radical, in which one C atom in the ring is replaced by S, O or $NR^{16}$, where $R^{16}$ is H; or $C_1$–$C_{10}$-alkyl, $C_2$–$C_{10}$-alkenyl or $C_2$–$C_{10}$-alkinyl, in each case branched or unbranched and mono- or polysubstituted or unsubstituted; or alkylaryl, aryl or heteroaryl, in each case mono- or polysubstituted or unsubstituted; in particular

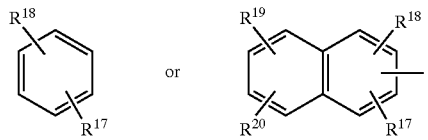

wherein $R^{17}$, $R^{18}$, $R^{19}$ and $R^{20}$ independently of one another are $R^{21}$ or $ZR^{21}$, whereing Z is $C_1$–$C_{10}$-alkyl, $C_2$–$C_{10}$-alkenyl or $C_2$–$C_{10}$-alkinyl, in each case branched or unbranched and mono- or polysubstituted or unsubstituted, and wherein $R^{21}$ is H; F; Cl; Br; I; CN; $NO_2$; $C_1$–$C_{18}$-alkyl, $C_2$–$C_{18}$-alkenyl or $C_2$–$C_{18}$-alkinyl, in each case branched or unbranched and mono- or polysubstituted or unsubstituted; $C_3$–$C_7$-cycloalkyl, saturated or unsaturated and mono- or polysubstituted or unsubstituted, or a corresponding heterocyclic radical, in which one C atom in the ring is replaced by S, O or $NR^{22}$, where $R^{22}$ is H; or $C_1$–$C_{10}$-alkyl, $C_2$–$C_{10}$-alkenyl or $C_2$–$C_{10}$-alkinyl, in each case branched or unbranched and mono- or polysubstituted or unsubstituted;

or alkylaryl, aryl or heteroaryl, in each case mono- or polysubstituted or unsubstituted;

$OR^{23}$, $OC(O)R^{23}$, $OC(O)OR^{23}$, $OC(S)R^{23}$, $C(O)R^{23}$, $C(O)OR^{23}$, $C(S)R^{23}$, $C(S)OR^{23}$, $SR^{23}$, $S(O)R^{23}$ or $S(O_2)R^{23}$, wherein $R^{23}$ is H; or $C_1$–$C_{18}$-alkyl, $C_2$–$C_{18}$-alkenyl or $C_2$–$C_{18}$-alkinyl, in each case branched or unbranched and mono- or polysubstituted or unsubstituted; $C_3$–$C_7$-cycloalkyl, saturated or unsaturated and mono- or polysubstituted or unsubstituted, or a corresponding heterocyclic radical, in which one C atom in the ring is replaced by S, O or $NR^{24}$, where $R^{24}$ is H; or $C_1$–$C_{10}$-alkyl, $C_2$–$C_{10}$-alkenyl or $C_2$–$C_{10}$-alkinyl, in each case branched or unbranched and mono- or polysubstituted or unsubstituted; alkylaryl, saturated or unsaturated and mono- or polysubstituted or unsubstituted; or aryl or heteroaryl, in each case mono- or polysubstituted or unsubstituted;

$NR^{25}R^{26}$, $NR^{25}C(O)R^{26}$, $C(O)NR^{25}R^{26}$ or $S(O_2)NR^{25}R^{26}$, wherein $R^{25}$ and $R^{26}$ independently of one another are H; $C_1$–$C_{18}$-alkyl, $C_2$–$C_{18}$-alkenyl or $C_2$–$C_{18}$-alkinyl, in each case branched or unbranched and mono- or polysubstituted or unsubstituted; $C_3$–$C_7$-cycloalkyl, saturated or unsaturated and mono- or polysubstituted or unsubstituted, or a corresponding heterocyclic radical, in which one C atom in the ring is replaced by S, O or $NR^{27}$, where $R^{27}$ is H; or $C_1$–$C_{10}$-alkyl, $C_2$–$C_{10}$-alkenyl or $C_2$–$C_{10}$-alkinyl, in each case branched or unbranched and mono- or polysubstituted or unsubstituted;

alkylaryl, saturated or unsaturated and mono- or polysubstituted or unsubstituted; or aryl or heteroaryl, in each case mono- or polysubstituted or unsubstituted; or wherein $R^{25}$ and $R^{26}$ together form a $C_3-C_7$-cycloalkyl, saturated or unsaturated and mono- or polysubstituted or unsubstituted, or a corresponding heterocyclic radical, in which one C atom in the ring is replaced by S, O or $NR^{27}$, where $R^{27}$ is H; or $C_1-C_{10}$-alkyl, $C_2-C_{10}$-alkenyl or $C_2-C_{10}$-alkinyl, in each case branched or unbranched and mono- or polysubstituted or unsubstituted.

In connection with alkyl, alkenyl, alkinyl and cycloalkyl and the "corresponding heterocyclic radical," the term substituted in the context of this invention is understood as meaning the replacement of a hydrogen radical by F, Cl, Br, I, $NH_2$, SH or OH; and polysubstituted radicals is understood as meaning radicals which are substituted more than once either on different or on the same atom, for example three times on the same C atom, as in the case of $CF_3$, or at different places, as in the case of —CH(OH)—CH=CH—$CHCl_2$.

Furthermore, —C(O)— denotes

which also applies to —C(S)— or —S(O)— and —S($O_2$)—.

The term "$C_1-C_8$-alkyl" or "$C_1-C_{10}$-alkyl" in the context of this invention denotes hydrocarbons having 1 to 8, or 1 to 10 carbon atoms respectively. Examples which may be mentioned are methyl, ethyl, propyl, isopropyl, n-butane, sec-butyl, tert-butyl, n-pentane, neopentyl, n-hexane, n-heptane, n-octane, n-nonane or n-decane.

The term "$C_1-C_{18}$-alkyl" in the context of this invention denotes hydrocarbons having 1 to 18 carbon atoms. Examples which may be mentioned are methyl, ethyl, propyl, isopropyl, n-butane, sec-butyl, tert-butyl, n-pentane, neopentyl, n-hexane, n-heptane, n-octane, n-nonane, n-decane, n-undecane, n-dodecane, n-tridecane, n-tetradecane, n-pentadecane, n-hexadecane, n-heptadecane or n-octadecane, unsubstituted or mono or polysubstituted.

The term "$C_2-C_{10}$-alkenyl" or "$C_2-C_{10}$-alkinyl" or "$C_2-C_{18}$-alkenyl" or "$C_2-C_{18}$-alkinyl" in the context of this invention denotes hydrocarbons having 2 to 8 or 2 to 18 carbon atoms respectively. Examples which may be mentioned are propenyl, butenyl, pentenyl, hexenyl, heptenyl or octenyl, unsubstituted or mono or polysubstituted, or propinyl, butinyl, pentinyl, hexinyl, heptinyl or octinyl, unsubstituted or mono or polysubstituted.

The term $C_3-C_7$-cycloalkyl in the context of this invention denotes cyclic hydrocarbons having 3 to 7 carbon atoms in the ring. Examples which may be mentioned are cyclopropyl, cyclobutyl, cyclopentyl, cyclohexyl, cycloheptyl, cyclohexenyl or cycloheptenyl, saturated or unsaturated and unsubstituted or mono- or polysubstituted. In the context of the invention a "corresponding heterocyclic radical" is understood as meaning a $C_3-C_7$-cycloalkyl in which one C atom in the ring is replaced by S, O or N. Examples which may be mentioned for this are pyrrolidine, pyran, thiolane, piperidine or tetrahydrofuran.

The term "aryl" in the context of this invention denotes phenyls or naphthyls.

The term "alkylaryl" in the context of this invention denotes aryls substituted by at least a $C_1-C_{10}$-alkylene, the terms aryl and alkyl having the same meaning as above. In this group benzaryl may be mentioned in particular.

The term "heteroaryl" in the context of this invention denotes a 5- or 6-membered aromatic compound which is optionally provided with a fused-on ring system and contain one or two heteroatoms selected from the groups consisting of nitrogen, oxygen and sulfur. Examples which may be mentioned in this group are furan, thiophene, pyrrole, pyridine, pyrimidine, quinoline, isoquinoline, phthalazine or quinazoline.

In respect of aryl, alkylaryl or heteroaryl, mono- or polysubstituted in the context of this invention is understood as meaning substitution of the ring system on one or more atoms by F; Cl; Br; I; $NH_2$; SH; OH; $CF_3$; or mono- or polysubstituted or unsubstituted $C_1-C_6$-alkyl, $C_1-C_6$-alkoxy, $C_2-C_8$-alkenyl, $C_2-C_8$-alkinyl; or aryl, in particular phenyl.

The phrase "Salt formed with a physiologically tolerated acid" in the context of this invention is understood as meaning salts of the particular active compound with inorganic or organic acids which are physiologically tolerated—in particular when used in humans and/or other mammals. Hydrochloride salts are particularly preferred.

Preferably, in formula I or Ia, $R^2$ and $R^3$ have different meanings and/or $R^3$ is H or $CH_3$, preferably H, while $R^1$, $R^{1'}$, $R^2$, $R^4$, $R^5$ and X are as defined above.

More preferably, in formula I or Ia, $R^2$ is

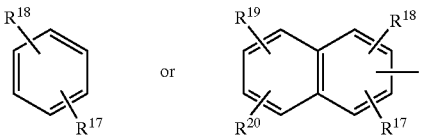

wherein $R^{17}$, $R^{18}$, $R^{19}$ and $R^{20}$, as well as $R^1$, $R^{1'}$, $R^3$, $R^4$, $R^5$ and X have meanings as defined above.

Preferably $R^2$ is a $C_{1-3}$-alkyl.

In another preferred embodiment in formula I or Ia, $R^2$ is

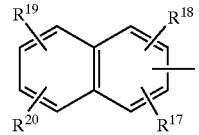

and $R^{19}$ and $R^{20}$ are H, while $R^1$, $R^{1'}$, $R^3$, $R^4$, $R^5$, X and $R^{17}$ and $R^{18}$ are as defined above.

In a further preferred embodiment, aminomethyl-phenyl-in formula I or Ia according to the invention, $R^2$ is

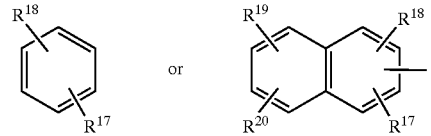

wherein $R^{17}$ and $R^{18}$ have a different meaning and/or $R^{18}$ is $R^{21}$, wherein $R^{21}$ is H, F, Cl, Br, I, $CF_3$ or $OR^{23}$, where $R^{23}$ is H, methyl ethyl, propyl, isopropyl, butyl or isobutyl, while $R^1$, $R^{1'}$, $R^3$, $R^4$, $R^5$ and X, as well as $R^{17}$, $R^{19}$ and $R^{20}$ have one of the meanings defined above.

More preferably, in formula I or Ia according to the invention, $R^2$ is

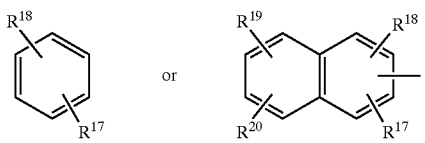

wherein R$^{17}$ is
R$^{21}$, wherein R$^{21}$ is
H, F, Cl, Br, I, CF$_3$, OR$^{23}$, OC(O)R$^{23}$, C(O)R$^{23}$ or C(O)OR$^{23}$, preferably H, F, Cl, C(O)OR$^{23}$, wherein R$^{23}$ is
H; or C$_1$–C$_6$-alkyl, C$_2$–C$_8$-alkenyl or C$_2$–C$_8$-alkinyl, in particular C$_1$–C$_4$-alkyl, branched or unbranched and mono- or polysubstituted or unsubstituted; preferably H, methyl ethyl, propyl, isopropyl, butyl or isobutyl, in particular H, CH$_3$, C$_2$H$_5$ or isobutyl;
or C(O)NR$^{25}$R$^{26}$, wherein R$^{25}$ and R$^{26}$ independently of one another are
H; 0; or C$_1$–C$_{18}$-alkyl, in particular C$_1$–C$_4$-alkyl, branched or unbranched, saturated or unsaturated and mono- or polysubstituted or unsubstituted; preferably H, methyl, ethyl, propyl, isopropyl, butyl or isobutyl, in particular C$_2$H$_5$; or
ZR$^{21}$, where Z is CH$_2$ or C$_2$H$_4$, preferably CH$_2$, wherein R$^{21}$ is
OR$^{23}$, OC(O)R$^{23}$, C(O)R$^{23}$ or C(O)OR$^{23}$, preferably OR$^{23}$, wherein R$^{23}$ is
H; or C$_1$–C$_6$-alkyl, C$_2$–C$_8$-alkenyl or C$_2$–C$_8$-alkinyl, in particular C$_1$–C$_4$-alkyl, branched or unbranched and mono- or polysubstituted or unsubstituted, preferably H, methyl, ethyl, propyl, isopropyl, butyl or isobutyl, in particular H;
C(O)NR$^{25}$R$^{26}$, wherein R$^{25}$ and R$^{26}$ independently of one another are chosen from
H, O, C$_1$–C$_{18}$-alkyl, in particular C$_1$–C$_4$-alkyl, branched or unbranched, saturated or unsaturated and mono- or polysubstituted or unsubstituted, preferably H, methyl ethyl, propyl, isopropyl, butyl or isobutyl;
while R$^1$, R$^{1'}$, R$^3$, R$^4$, R$^5$ and X and R$^{18}$, R$^{19}$ and R$^{20}$ are as defined above.

In a particularly preferred embodiment in formula I or Ia according to the invention
R$^1$ is
H, F, Cl, Br, I, CF$_3$, SCH$_3$ or OR$^6$, preferably OR$^6$, wherein R$^6$ is
H; or C$_1$–C$_4$-alkyl, branched or unbranched and mono- or polysubstituted or unsubstituted; preferably H or CH$_3$; and/or
R$^1$ is
H, F, Cl, SCH$_3$ or OCH$_3$, preferably H and/or
X is
H, F, Br, I, Cl or OR$^7$, preferably H, F, Cl or OR$^7$, where R$^7$ is H or CH$_3$, preferably H; or
if the compound contains no X, according to formula Ia a double bond is formed between C atom A and C atom B or C atom B and C atom C; and/or
R$^4$ and R$^5$ independently of one another are
C$_1$–C$_4$-alkyl, branched or unbranched and mono- or polysubstituted or unsubstituted, preferably CH$_3$,
while R$^2$ and R$^3$ have one of the above-defined meanings.

The following substituted aminomethyl-phenyl-cyclohexane derivatives according to the invention are particularly preferred:

rac-cis-E-[-4-benzylidene-2-(3-methoxy-phenyl)-cyclohexylmethyl]-dimethylamine,
rac-trans-E-[4-benzylidene-2-(3-methoxy-phenyl)-cyclohexylmethyl]-dimethylamine,
rac-trans-Z-[4-benzylidene-2-(3-methoxy-phenyl)-cyclohexylmethyl]-dimethylamine,
rac-cis-Z-[4-benzylidene-2-(3-methoxy-phenyl)-cyclohexylmethyl]-dimethylamine,
rac-cis-E-3-[4-dimethylaminomethyl-3-(3-methoxy-phenyl)-cyclohexylidenemethyl]-benzoic acid methyl ester,
rac-cis-Z-3-[4-dimethylaminomethyl-3-(3-methoxy-phenyl)-cyclohexylidenemethyl]-benzoic acid methyl ester,
rac-trans-Z-3-[4-dimethylaminomethyl-3-(3-methoxy-phenyl)-cyclohexylidenemethyl]-benzoic acid methyl ester,
rac-trans-E-3-[4-dimethylaminomethyl-3-(3-methoxy-phenyl)-cyclohexylidenemethyl]-benzoic acid methyl ester,
Z-3-[4-dimethylaminomethyl-3-(3-methoxy-phenyl)-2-methyl-cyclohex-2-enylidenemethyl]-benzoic acid methyl ester,
E-3-[4-dimethylaminomethyl-3-(3-methoxy-phenyl)-2-methyl-cyclohex-2-enylidenemethyl]-benzoic acid methyl ester,
Z-3-[4-dimethylaminomethyl-3-(3-methoxy-phenyl)-2-methyl-cyclohex-2-enylidenemethyl]-naphthalene-1-carboxylic acid ethyl ester,
E-3-[4-dimethylaminomethyl-3-(3-methoxy-phenyl)-2-methyl-cyclohex-2-enylidenemethyl]-naphthalene-1-carboxylic acid ethyl ester,
Z-3-[4-dimethylaminomethyl-3-(3-methoxy-phenyl)-cyclohexylidenemethyl]-2-fluoro-benzoic acid ethyl ester,
Z-3-[4-dimethylaminomethyl-3-(3-methoxy-phenyl)-cyclohex-2-enylidenemethyl]-benzoic acid,
E-3-[4-dimethylaminomethyl-3-(3-methoxy-phenyl)-cyclohex-2-enylidenemethyl]-benzoic acid,
E-{3-[4-dimethylaminomethyl-3-(3-methoxy-phenyl)-cyclohex-2-enylidenemethyl]-phenyl}-methanol,
rac-trans-Z-3-[4-dimethylaminomethyl-3-(3-methoxy-phenyl)-cyclohexylidenemethyl]-benzoic acid,
rac-trans-E-3-[4-dimethylaminomethyl-3-(3-methoxy-phenyl)-cyclohexylidenemethyl]-benzoic acid,
rac-trans-E-[3-(2-dimethylaminomethyl-5-(3-hydroxymethyl-benzylidene)-cyclohexyl)-phenol,
rac-trans-E-3-(5-benzylidene-2-dimethylaminomethyl-cyclohexyl)-phenol,
E-3-[4-dimethylaminomethyl-3-(3-methoxy-phenyl)-cyclohex-2-enylidenemethyl]-benzoic acid tert-butyl ester,
E-3-[6-dimethylaminomethyl-3-(3-hydroxymethyl-benzylidene)-cyclohex-1-enyl]-phenol,
rac-trans-Z-3-(5-benzylidene-2-dimethylaminomethyl-cyclohexyl)-phenol,
Z-3-[2-dimethylaminomethyl-5-(3-hydroxymethyl-benzylidene)-cyclohex-1-enyl]-phenol,
Z-{3-[4-dimethylaminomethyl-3-(3-methoxy-phenyl)-cyclohex-2-enylidenemethyl]-phenyl}-methanol,
rac-cis-E-3-[4-dimethylaminomethyl-3-(3-methoxy-phenyl)-cyclohexylidenemethyl]-benzoic acid, rac-cis-Z-3-[4-dimethylaminomethyl-3-(3-methoxy-phenyl)-cyclohexylidenemethyl]-benzoic acid, rac-trans-E-3-[4-dimethylaminomethyl-3-(3-methoxy-phenyl)-cyclohexylidenemethyl]-benzoic acid tert-butyl ester, rac-trans-E-[3-[4-dimethylaminomethyl-3-(3-methoxy-phenyl)-cyclohexylidenemethyl)-phenyl)-methanol], rac-cis-Z-3-[4-dimethylaminomethyl-3-(3-methoxy-phenyl)-cyclohexylidenemethyl]-benzoic acid ethyl ester, E-3-[4-dimethylaminomethyl-3-(3-methoxy-phenyl)-cyclohex-2-enylidenemethyl]-N,N-diethyl-benzamide rac-trans-E-3-[4-dimethylaminomethyl-3-(3-methoxy-phenyl)-cyclohex-2-enylidenemethyl]-N,N-diethyl-benzamide, E-3-[4-dimethylaminomethyl-3-(3-methoxy-phenyl)-cyclohex-2-enylidenemethyl]-benzoic acid ethyl ester, Z-3-[4-dimethylaminomethyl-3-(3-methoxy-phenyl)-cyclohex-2-enylidenemethyl]-N,N-diethyl-benzamide, rac-cis-E-3-[4-dimethylaminomethyl-3-(3-methoxy-phenyl)-cyclohexylidenemethyl]-N,N-diethyl-benzamide, rac-trans-Z-3-[4-dimethylaminomethyl-3-(3-methoxy-phenyl)-cyclohexylidenemethyl]-N,N-diethyl-benzamide, E-3-[4-dimethylaminomethyl-3-(3-hydroxy-phenyl)-cyclohex-2-enylidenemethyl]-benzoic acid methyl ester, Z-3-[4-dimethylaminomethyl-3-(3-hydroxy-phenyl)-cyclohex-2-enylidenemethyl]-benzoic acid methyl ester, Z-3-[4-dimethylaminomethyl-3-(3-methoxy-phenyl)-cyclohex-2-enylidenemethyl]-benzoic acid isobutyl ester, Z-3-[6-dimethylaminomethyl-3-(3-hydroxymethyl-benzylidene)-cyclohex-1-enyl]-phenol, Z-[4-(4-chloro-benzylidene)-2-(3-methoxy-phenyl)-cyclohex-2-enylmethyl]-dimethyl-amine, E-[4-(4-fluoro-benzylidene)-2-(3-methoxy-phenyl)-cyclohex-2-enylmethyl]-dimethyl-amine, Z-[4-(4-fluoro-benzylidene)-2-(3-methoxy-phenyl)-cyclohex-2-enylmethyl]-dimethyl-amine, E-3-[6-dimethylaminomethyl-3-(4-fluoro-benzylidene)-cyclohex-1-enyl]-phenol, Z-3-[6-dimethylaminomethyl-3-(4-fluoro-benzylidene)-cyclohex-1-enyl]-phenol, E-[4-(4-chloro-benzylidene)-2-(3-methoxy-phenyl)-cyclohex-2-enylmethyl]-dimethyl-amine, E-3-[3-(4-chloro-benzylidene)-6-dimethylaminomethyl-cyclohex-1-enyl]-phenol, Z-3-[4-dimethylaminomethyl-3-(3-hydroxy-phenyl)-cyclohex-2-enylidenemethyl]-benzoic acid methyl ester, E-3-[4-dimethylaminomethyl-3-(3-hydroxy-phenyl)-cyclohex-2-enylidenemethyl]-benzoic acid, rac-cis-E-3-[4-dimethylaminomethyl-3-(3-hydroxy-phenyl)-cyclohexylidenemethyl]-benzoic acid methyl ester, rac-cis-Z-3-[4-dimethylaminomethyl-3-(3-hydroxy-phenyl)-cyclohexylidenemethyl]-benzoic acid methyl ester, rac-trans-Z-3-[4-dimethylaminomethyl-3-(3-hydroxy-phenyl)-cyclohexylidenemethyl]-benzoic acid, rac-trans-E-[4-dimethylaminomethyl-3-(3-hydroxy-phenyl)-cyclohexylidenemethyl]-benzoic acid, rac-cis-Z-3-[4-dimethylaminomethyl-3-(3-hydroxy-phenyl)-cyclohexylidenemethyl]-benzoic acid, rac-cis-Z-3-[4-dimethylaminomethyl-3-hydroxy-3-(3-methoxy-phenyl)-cyclohexylidenemethyl]-benzoic acid methyl ester, rac-cis-E-3-[3-chloro-4-dimethylaminomethyl-3-(3-methoxy-phenyl)-cyclohexylidenemethyl]-benzoic acid methyl ester, rac-cis-E-3-[4-dimethylaminomethyl-3-hydroxy-3-(3-methoxy-phenyl)-cyclohexylidenemethyl]-benzoic acid methyl ester, rac-cis-Z-3-[4-dimethylaminomethyl-3-hydroxy-3-(3-methoxy-phenyl)-cyclohexylidenemethyl]-benzoic acid methyl ester, (+)-trans-E-3-[4-dimethylaminomethyl-3-(3-methoxy-phenyl)-cyclohexylidenemethyl]-benzoic acid, (−)-trans-E-3-[4-dimethylaminomethyl-3-(3-methoxy-phenyl)-cyclohexylidenemethyl]-benzoic acid, rac-trans-E-3-(4-dimethylaminomethyl-3-phenyl-cyclohexylidenemethyl)-benzoic acid methyl ester, rac-trans-Z-3-(4-dimethylaminomethyl-3-phenyl-cyclohexylidenemethyl)-benzoic acid methyl ester, rac-cis-E-3-(4-dimethylaminomethyl-3-phenyl-cyclohexylidenemethyl)-benzoic acid, rac-cis-E-3-(4-dimethylaminomethyl-3-phenyl-cyclohexylidenemethyl)-benzoic acid, rac-trans-Z-3-(4-dimethylaminomethyl-3-phenyl-cyclohexylidenemethyl)benzoic acid, rac-trans-E-3-(4-dimethylaminomethyl-3-phenyl-cyclohexylidenemethyl)-benzoic acid, rac-trans-E-3-[4-dimethylaminomethyl-3-(3-trifluoromethyl-phenyl)-cyclohexylidenemethyl]-benzoic acid, rac-trans-Z-3-[4-dimethylaminomethyl-3-(3-trifluoromethyl-phenyl)-cyclohexylidenemethyl]-benzoic acid, rac-trans-E-3-[4-dimethylaminomethyl-3-(3-fluoro-phenyl)-cyclohexylidenemethyl]-benzoic acid methyl ester, rac-trans-Z-3-[4-dimethylaminomethyl-3-(3-fluoro-phenyl)-cyclohexylidenemethyl]benzoic acid methyl ester, rac-cis-E-3-[4-dimethylaminomethyl-3-(3-fluoro-phenyl)-cyclohexylidenemethyl]-benzoic acid methyl ester, rac-trans-E-3-[4-dimethylaminomethyl-3-(3-fluoro-phenyl)-cyclohexylidenemethyl]-benzoic acid, rac-trans-Z-3-[4-dimethylaminomethyl-3-(3-fluoro-phenyl)-cyclohexylidenemethyl]-benzoic acid, rac-cis-E-3-[4-dimethylaminomethyl-3-(3-fluoro-phenyl)-cyclohexylidenemethyl]-benzoic acid E-[4-ethylidene-2-(3-methoxy-phenyl)-cyclohex-2-enylmethyl]-dimethylamine

[4-isopropylidene-2-(3-methoxy-phenyl)-cyclohex-2-enylmethyl]-dimethylamine,

E-[2-(3-methoxy-phenyl)-4-propylidene-cyclohex-2-enylmethyl]-dimethylamine,

E-[4-butylidene-2-(3-methoxy-phenyl)-cyclohex-2-enylmethyl]-dimethylamine and salts thereof, in particular hydrochloride salts.

The invention also provides a process for the preparation of substituted aminomethyl-phenyl-cyclohexane derivatives of the formula I or Ia

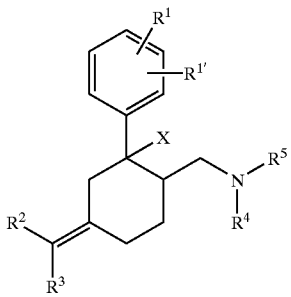
I

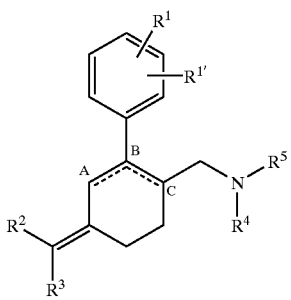
Ia in which $R^1$, $R^{1'}$, $R^2$, $R^3$, $R^4$, $R^5$ and X are as previously defined. According to the present invention cyclohexanones of the formula II or IIa

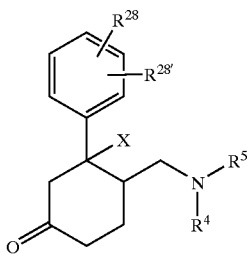
II

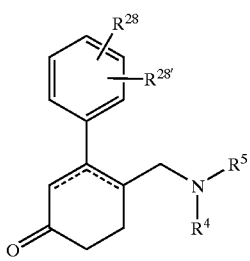
IIa in which $R^4$, $R^5$ and X are as defined above, $R^{28}$ is as defined in the definition of $R^1$, and $R^{28'}$is as defined in the definition of $R^{1'}$, are reacted in a Wittig reaction in an organic solvent in the presence of a base with alkyltriphenylphosphonium salts of the formula III

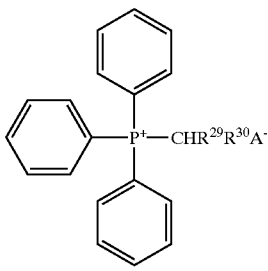
III wherein A denotes chloride or bromide and, independently of one another, $R^{29}$ is as defined in the above definition of $R^2$ and $R^{30}$ is as defined in the above definition of $R^3$.

Preferred organic solvents here are benzene, toluene or a chlorinated hydrocarbon, and potassium tert-butylate or sodium hydride are preferably used as the base. Furthermore, the reaction temperature, in particular during the Wittig reaction, is preferably kept between 50° C. and 90° C.

OH, SH and $NH_2$ groups can undergo undesirable side reactions under the reaction conditions mentioned. It is therefore preferable to provide these with protective groups, or in the case of $NH_2$ to replace it by $NO_2$, and to remove the protective group or reduce the $NO_2$ group after the Wittig reaction. The present invention therefore also provides a modification of the process described above in which in $R^{28}$ and/or $R^{28'}$ according to formula II or Ia and/or $R^{29}$ and/or $R^{30}$ according to formula III at least one OH group has been replaced by an $OSi(Ph)_2$tert-but group, at least one SH group has been replaced by an S-p-methoxybenzyl group and/or at least one $NH_2$ group has been replaced by an $NO_2$ group and, after conclusion of the Wittig reaction, at least one $OSi(Ph)_2$tert-but group is split off with tetrabutylammonium fluoride in tetrahydrofuran and/or at least one p-methoxybenzyl group is split off with a metal amine, preferably sodium amine, and/or at least one $NO_2$ group is reduced to $NH_2$.

Furthermore, carboxylic acid or thiocarboxylic acid groups are not stable under certain circumstances under the conditions of the Wittig reaction, so that it is preferable to react methyl esters thereof in the Wittig reaction and then to hydrolyse the process product from the Wittig reaction with KOH solution or NaOH solution in methanol at 40° C.–60° C. The invention therefore also provides a modification of the processes described above in which, after the Wittig reaction, a process product with at least one $C(O)OCH_3$, $OC(O)OCH_3$ and/or $C(S)OCH_3$ group is hydrolyzed with KOH solution or NaOH solution in methanol at 40° C.–60° C.

The reactions proceed specifically and with high yields. Nevertheless, purification of the compounds obtained in the individual reaction sequences, in particular of the end product, is usually necessary. The purification is preferably carried out via crystallization or chromatographic methods, in particular column chromatography.

The compounds of formula I or Ia can be converted into their salts in a manner well-known to those of ordinary skill in the art with physiologically tolerated acids, such as hydrochloric acid, hydrobromic acid, sulfuric acid, methanesulfonic acid, formic acid, acetic acid, oxalic acid, succinic acid, tartaric acid, mandelic acid, fumaric acid, lactic acid, citric acid, glutamic acid and/or aspartic acid. The salt formation is preferably carried out in a solvent, such as diisopropyl ether, acetic acid alkyl esters, acetone and/or 2-butanone. Trimethylchlorosilane in aqueous solution is particularly suitable for preparation of the hydrochlorides.

The cyclohexanones of formulae II and IIa are prepared by first reacting 3,3-dimethyl-1,5-dioxa-spiro[5.5]undecan-8-one with immonium salts of the formula IV or with formaldehyde and an amine of the formula V. The Mannich bases obtained in this way are then reacted with an organometallic compound of the formula VI, in which Z denotes MgCl, MgBr, MgI or lithium. The reaction of the Mannich bases with a Grignard compound of the formula VI, in which Z denotes MgCl, MgBr or MgI, or with an organolithium compound of the formula VI, in which Z is Li, can be carried out in an aliphatic ether, for example diethyl ether and/or tetrahydrofuran, at temperatures of between –70° C. and 60° C. The reaction with a Grignard compound of the formula VI can be carried out with or without the addition of an entraining reagent. If an entraining reagent is employed, 1,2-dibromoethane is preferred.

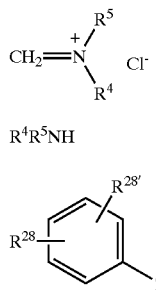

IV $R^4R^5NH$      V

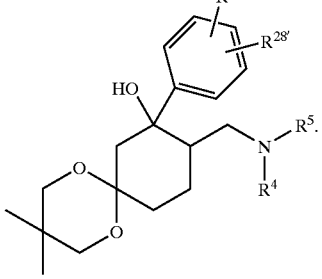    VI

Products of the general formula VII are first obtained in this way.

VII

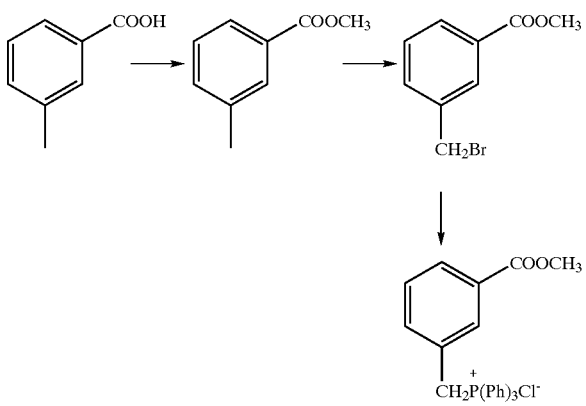

Compounds of the formula IIa are obtained by reacting products of the general formula VII with an acid, for example hydrochloric acid, formic acid or acetic acid, at room temperature. Subsequent hydrogenation of the products obtained in this way with catalytically activated hydrogen, platinum or palladium absorbed on a support material, such as active charcoal, serving as the catalyst, leads to compounds of the formula II where X is H. The hydrogenation is carried out in a solvent, such as ethyl acetate or a $C_1$–$C_4$-alkyl alcohol, under pressures of 0.1 to 10 bar and at temperatures of 20° C. to 80° C.

Compounds of the general formula II where X is OH are obtained by reacting products of the general formula VII with acids, for example hydrochloric acid, at temperatures of between 5° C. and 10° C.

Compounds of the general formula II where X is F, Cl, Br, I or $CF_3$ are obtained by replacement of OH by F or Cl or Br or I or $CF_3$ by processes well known to those ordinarily skilled in the art.

Compounds of the general formula II where X is $OR^7$ are obtained by etherification of the OH group with a halide of the formula VIII;

$R^7Cl$      VIII.

Compounds of the general formula II where X is OC(O)$R^7$ are obtained by esterification of the OH group with an acid chloride of the formula IX;

$R^7COCl$      IX.

Most of the substituted alkyltriphenylphosphonium salts used in the preparation process are commercially obtainable. However, in some exceptional cases these must be synthesized. 3-(Benzoic acid methyl ester)-methyltriphenylphosphonium bromide may be mentioned as an example of the synthesis of the substituted alkyltriphenylphosphonium salts:

This is prepared as follows: 3-Toluic acid is converted with methanol in the presence of sulfuric acid into 3-toluic acid methyl ester, which reacts with N-bromosuccinimide to give 3-bromomethyl-benzoic acid methyl ester. Reaction of bromomethyl-benzoic acid methyl ester with triphenylphosphane finally leads to 3-(benzoic acid methyl ester)-methyltriphenylphosphonium bromide.

The substituted aminomethyl-phenyl-cyclohexane derivatives according to the invention are toxicologically acceptable so that they are suitable as a pharmaceutical active compound in medicaments.

The invention therefore also provides medicaments which comprise, as the active compound, at least one substituted aminomethyl-phenyl-cyclohexane derivative of the general formula I or Ia

I

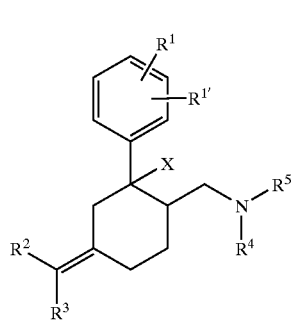

-continued

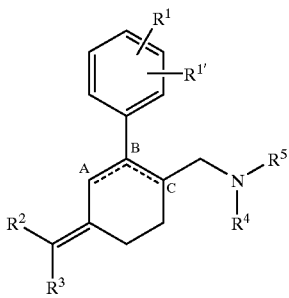

Ia in which $R^1$, $R^{1'}$, $R^2$, $R^3$, $R^4$, $R^5$ and X have one of the meanings mentioned in claim 1, in the form of its diastereomers or enantiomers and of its free base or of a salt formed with a physiologically tolerated acid, in particular a hydrochloride salt.

Medicaments which comprise as the active compound at least one substituted aminomethyl-phenyl-cyclohexane derivative chosen from the following group are particularly preferred here:

rac-cis-E-[-4-benzylidene-2-(3-methoxy-phenyl)-cyclohexylmethyl]-dimethylamine, rac-trans-E-[4-benzylidene-2-(3-methoxy-phenyl)-cyclohexylmethyl]-dimethylamine, rac-trans-Z-[4-benzylidene-2-(3-methoxy-phenyl)-cyclohexylmethyl]-dimethylamine, rac-cis-Z-[4-benzylidene-2-(3-methoxy-phenyl)-cyclohexylmethyl]-dimethylamine, rac-cis-E-3-[4-dimethylaminomethyl-3-(3-methoxy-phenyl)-cyclohexylidenemethyl]-benzoic acid methyl ester, rac-cis-Z-3-[4-dimethylaminomethyl-3-(3-methoxy-phenyl)-cyclohexylidenemethyl]-benzoic acid methyl ester, rac-trans-Z-3-[4-dimethylaminomethyl-3-(3-methoxy-phenyl)-cyclohexylidenemethyl]-benzoic acid methyl ester, rac-trans-E-3-[4-dimethylaminomethyl-3-(3-methoxy-phenyl)-cyclohexylidenemethyl]-benzoic acid methyl ester, Z-3-[4-dimethylaminomethyl-3-(3-methoxy-phenyl)-2-methyl-cyclohex-2-enylidenemethyl]-benzoic acid methyl ester, E-3-[4-dimethylaminomethyl-3-(3-methoxy-phenyl)-2-methyl-cyclohex-2-enylidenemethyl]-benzoic acid methyl ester, Z-3-[4-dimethylaminomethyl-3-(3-methoxy-phenyl)-2-methyl-cyclohex-2-enylidenemethyl]-naphthalene-1-carboxylic acid ethyl ester, E-3-[4-dimethylaminomethyl-3-(3-methoxy-phenyl)-2-methyl-cyclohex-2-enylidenemethyl]-naphthalene-1-carboxylic acid ethyl ester, Z-3-[4-dimethylaminomethyl-3-(3-methoxy-phenyl)-cyclohexylidenemethyl]-2-fluoro-benzoic acid ethyl ester, Z-3-[4-dimethylaminomethyl-3-(3-methoxy-phenyl)-cyclohex-2-enylidenemethyl]-benzoic acid, E-3-[4-dimethylaminomethyl-3-(3-methoxy-phenyl)-cyclohex-2-enylidenemethyl]-benzoic acid, E-{3-[4-dimethylaminomethyl-3-(3-methoxy-phenyl)-cyclohex-2-enylidenemethyl]-phenyl}-methanol, rac-trans-Z-3-[4-dimethylaminomethyl-3-(3-methoxy-phenyl)-cyclohexylidenemethyl]-benzoic acid, rac-trans-E-3-[4-dimethylaminomethyl-3-(3-methoxy-phenyl)-cyclohexylidenemethyl]-benzoic acid, rac-trans-E-[3-(2-dimethylaminomethyl-5-(3-hydroxymethyl-benzylidene)-cyclohexyl)-phenol, rac-trans-E-3-(5-benzylidene-2-dimethylaminomethyl-cyclohexyl)-phenol, E-3-[4-dimethylaminomethyl-3-(3-methoxy-phenyl)-cyclohex-2-enylidenemethyl]-benzoic acid tert-butyl ester, E-3-[6-dimethylaminomethyl-3-(3-hydroxymethyl-benzylidene)-cyclohex-1-enyl]-phenol, rac-trans-Z-3-(5-benzylidene-2-dimethylaminomethyl-cyclohexyl)-phenol, Z-3-[2-dimethylaminomethyl-5-(3-hydroxymethyl-benzylidene)-cyclohex-1-enyl]-phenol, Z-{3-[4-dimethylaminomethyl-3-(3-methoxy-phenyl)-cyclohex-2-enylidenemethyl]-phenyl}-methanol, rac-cis-E-3-[4-dimethylaminomethyl-3-(3-methoxy-phenyl)-cyclohexylidenemethyl]-benzoic acid, rac-cis-Z-3-[4-dimethylaminomethyl-3-(3-methoxy-phenyl)-cyclohexylidenemethyl]-benzoic acid, rac-trans-E-3-[4-dimethylaminomethyl-3-(3-methoxy-phenyl)-cyclohexylidenemethyl]-benzoic acid tert-butyl ester, rac-trans-E-[3-[4-dimethylaminomethyl-3-(3-methoxy-phenyl)-cyclohexylidenemethyl)-phenyl)-methanol], rac-cis-Z-3-[4-dimethylaminomethyl-3-(3-methoxy-phenyl)-cyclohexylidenemethyl]-benzoic acid ethyl ester, E-3-[4-dimethylaminomethyl-3-(3-methoxy-phenyl)-cyclohex-2-enylidenemethyl]-N,N-diethyl-benzamide
rac-trans-E-3-[4-dimethylaminomethyl-3-(3-methoxy-phenyl)-cyclohex-2-enylidenemethyl]-N,N-diethyl-benzamide, E-3-[4-dimethylaminomethyl-3-(3-methoxy-phenyl)-cyclohex-2-enylidenemethyl]-benzoic acid ethyl ester,
Z-3-[4-dimethylaminomethyl-3-(3-methoxy-phenyl)-cyclohex-2-enylidenemethyl]-N,N-diethyl-benzamide, rac-cis-E-3-[4-dimethylaminomethyl-3-(3-methoxy-phenyl)-cyclohexylidenemethyl]-N,N-diethyl-benzamide, rac-trans-Z-3-[4-dimethylaminomethyl-3-(3-methoxy-phenyl)-cyclohexylidenemethyl]-N,N-diethyl-benzamide, E-3-[4-dimethylaminomethyl-3-(3-hydroxy-phenyl)-cyclohex-2-enylidenemethyl]-benzoic acid methyl ester, Z-3-[4-dimethylaminomethyl-3-(3-hydroxy-phenyl)-cyclohex-2-enylidenemethyl]-benzoic acid methyl ester, Z-3-[4-dimethylaminomethyl-3-(3-methoxy-phenyl)-cyclohex-2-enylidenemethyl]-benzoic acid isobutyl ester, Z-3-[6-dimethylaminomethyl-3-(3-hydroxymethyl-benzylidene)-cyclohex-1-enyl]-phenol, Z-[4-(4-chloro-benzylidene)-2-(3-methoxy-phenyl)-cyclohex-2-enylmethyl]-dimethyl-amine, E-[4-(4-fluoro-benzylidene)-2-(3-methoxy-phenyl)-cyclohex-2-enylmethyl]-dimethyl-amine, Z-[4-(4-fluoro-benzylidene)-2-(3-methoxy-phenyl)-cyclohex-2-enylmethyl]-dimethyl-amine, E-3-[6-dimethylaminomethyl-3-(4-fluoro-benzylidene)-cyclohex-1-enyl]-phenol, Z-3-[6-dimethylaminomethyl-3-(4-fluoro-benzylidene)-cyclohex-1-enyl]-phenol, E-[4-(4-chloro-benzylidene)-2-(3-methoxy-phenyl)-cyclohex-2-enylmethyl]-dimethyl-amine, E-3-[3-(4-chloro-benzylidene)-6-dimethylaminomethyl-cyclohex-1-enyl]-phenol, Z-3-[4-dimethylaminomethyl-3-(3-hydroxy-phenyl)-cyclohex-2-enylidenemethyl]-benzoic acid methyl ester, E-3-[4-dimethylaminomethyl-3-(3-hydroxy-phenyl)-cyclohex-2-enylidenemethyl]-benzoic acid, rac-cis-E-3-[4-dimethylaminomethyl-3-(3-hydroxy-phenyl)-cyclohexylidenemethyl]-benzoic acid methyl ester, rac-cis-Z-3-[4-dimethylaminomethyl-3-(3-hydroxy-phenyl)-cyclohexylidenemethyl]-benzoic acid methyl ester, rac-trans-Z-3-[4-dimethylaminomethyl-3-(3-hydroxy-phenyl)-cyclohexylidenemethyl]-benzoic acid, rac-trans-E-3-[4-dimethylaminomethyl-3-(3-hydroxy-phenyl)-cyclohexylidenemethyl]-benzoic acid, rac-cis-Z-3-[4-dimethylaminomethyl-3-(3-hydroxy-phenyl)-cyclohexylidenemethyl]-benzoic acid, rac-cis-Z-3-[4-dimethylaminomethyl-3-hydroxy-3-(3-methoxy-phenyl)-cyclohexylidenemethyl]-benzoic acid methyl ester, rac-cis-E-3-[3-chloro-4-dimethylaminomethyl-3-(3-methoxy-phenyl)-cyclohexylidenemethyl]-benzoic acid methyl ester, rac-cis-E-3-[4-dimethylaminomethyl-3-hydroxy-3-(3-methoxy-phenyl)-cyclohexylidenemethyl]-benzoic acid methyl ester, rac-cis-Z-3-[4-dimethylaminomethyl-3-hydroxy-3-(3-methoxy-phenyl)-cyclohexylidenemethyl]-benzoic acid methyl ester, (+)-trans-E-3-[4-dimethylaminomethyl-3-(3-methoxy-phenyl)-cyclohexylidenemethyl]-benzoic acid, (−)-trans-E-3-[4-dimethylaminomethyl-3-(3-methoxy-phenyl)-cyclohexylidenemethyl]-benzoic acid, rac-trans-E-3-(4-dimethylaminomethyl-3-phenyl-cyclohexylidenemethyl)-benzoic acid methyl ester, rac-trans-Z-3-(4-dimethylaminomethyl-3-phenyl-cyclohexylidenemethyl)-benzoic acid methyl ester, rac-cis-E-3-(4-dimethylaminomethyl-3-phenyl-cyclohexylidenemethyl)-benzoic acid, rac-cis-E-3-(4-dimethylaminomethyl-3-phenyl-cyclohexylidenemethyl)-benzoic acid, rac-trans-Z-3-(4-dimethylaminomethyl-3-phenyl-cyclohexylidenemethyl)benzoic acid, rac-trans-E-3-(4-dimethylaminomethyl-3-phenyl-cyclohexylidenemethyl)-benzoic acid, rac-trans-E-3-[4-dimethylaminomethyl-3-(3-triflluoromethyl-phenyl)-cyclohexylidenemethyl]-benzoic acid, rac-trans-Z-3-[4-dimethylaminomethyl-3-(3-trifluoromethyl-phenyl)-cyclohexylidenemethyl]-benzoic acid, rac-trans-E-3-[4-dimethylaminomethyl-3-(3-fluoro-phenyl)-cyclohexylidenemethyl]-benzoic acid methyl ester, rac-trans-Z-3-[4-dimethylaminomethyl-3-(3-fluoro-phenyl)-cyclohexylidenemethyl]benzoic acid methyl ester, rac-cis-E-3-[4-dimethylaminomethyl-3-(3-fluoro-phenyl)-cyclohexylidenemethyl]-benzoic acid methyl ester, rac-trans-E-3-[4-dimethylaminomethyl-3-(3-fluoro-phenyl)-cyclohexylidenemethyl]-benzoic acid, rac-trans-Z-3-[4-dimethylaminomethyl-3-(3-fluoro-phenyl)-cyclohexylidenemethyl]-benzoic acid, rac-cis-E-3-[4-dimethylaminomethyl-3-(3-fluoro-phenyl)-cyclohexylidenemethyl]-benzoic acid, E-[4-ethylidene-2-(3-methoxy-phenyl)-cyclohex-2-enylmethyl]-dimethylamine,

[4-isopropylidene-2-(3-methoxy-phenyl)-cyclohex-2-enylmethyl]-dimethylamine,

E-[2-(3-methoxy-phenyl)-4-propylidene-cyclohex-2-enylmethyl]-dimethylamine, and

E-[4-butylidene-2-(3-methoxy-phenyl)-cyclohex-2-enylmethyl]-dimethylamine, as a free base or in the form of a salt formed with a physiologically tolerated acid, in particular a hydrochloride salt.

The medicaments according to the invention comprise, in addition to at least one substituted aminomethyl-phenyl-cyclohexane derivative according to the invention, carrier materials, fillers, solvents, diluents, dyestuffs and/or binders and can be administered as liquid formulations such as injection solutions, drops or juices, or as semi-solid formulations, or as granules, tablets, pellets, patches, capsules, plasters or aerosols. The choice of auxiliary substances and the amounts thereof to be employed depends on whether the medicament is to be administered orally, perorally, parenterally, intravenously, intraperitoneally, intradermally, intramuscularly, intranasally, buccally, rectally or locally, for example on infections of the skin, the mucous membranes and the eyes. Formulations in the form of tablets, coated tablets, capsules, granules, drops, juices and syrups are suitable for oral administration, and solutions, suspensions, easily reconstitutable dry formulations and sprays are suitable for parenteral, topical and inhalatory administration. Substituted aminomethyl-phenyl-cyclohexane derivatives according to the invention in a depot in dissolved form or in a patch, optionally with the addition of agents which promote penetration through the skin, are suitable formulations for percutaneous administration. Formulation forms which can be used orally or percutaneously can release the substituted aminomethyl-phenyl-cyclohexane derivatives according to the invention in a delayed manner. The amount of active compound to be administered to the patient varies according to the body weight of the patient, the mode of administration, the indication and the severity of the disease. 50 to 500 mg/kg of at least one substituted aminomethyl-phenyl-cyclohexane derivative according to the invention are usually administered.

The substituted aminomethyl-phenyl-cyclohexane derivatives according to the invention are preferably employed for treatment of pain, so that the invention also provides the use of at least one substituted aminomethyl-phenyl-cyclohexane derivative of the general formula I or Ia

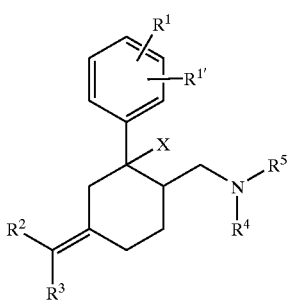

I

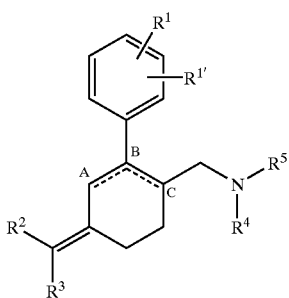

Ia in which R¹, R¹', R², R³, R⁴, R⁵ and X are as defined above, in the form of its diastereomers or enantiomers and of its free base or of a salt formed with a physiologically tolerated acid, in particular the hydrochloride salt, for the preparation of a medicament or a pharmaceutical composition for treatment of pain.

It has been found, surprisingly, that the substituted aminomethyl-phenyl-cyclohexane derivatives according to the invention are very suitable for further indications, in particular for treatment of urinary incontinence, itching and/or diarrhoea, and also in other indications. The present invention therefore also provides the use of at least one substituted aminomethyl-phenyl-cyclohexane derivative of the general formula I or Ia

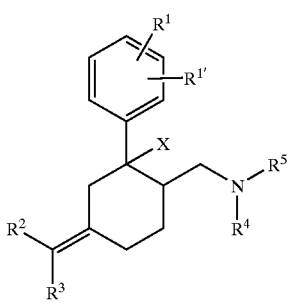

I

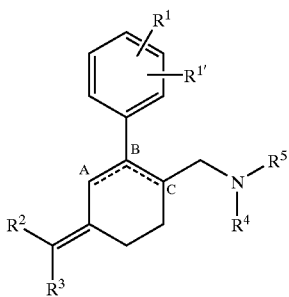

Ia in which R¹, R¹', R², R³, R⁴, R⁵ and X are as defined above, in the form of its diastereomers or enantiomers and of its free base or of a salt formed with a physiologically tolerated acid, in particular the hydrochloride salt, for the preparation of a medicament for treatment of inflammatory and allergic reactions, depression, drug and/or alcohol abuse, gastritis, cardiovascular diseases, respiratory tract diseases, coughing, mental illnesses and/or epilepsy, and in particular urinary incontinence, itching and/or diarrhoea.

The invention is explained further by examples in the following, without limiting it thereto.

EXAMPLES

The following examples show compounds according to the invention and the preparation thereof, and activity studies carried out therewith.

The following information generally applies:

The yields of the compounds prepared are not optimized.

All temperatures are uncorrected.

Silica gel 60 (0.040–0.063 mm) from E. Merck, Darmstadt was employed as the stationary phase for the column chromatography.

The thin layer chromatography studies were carried out with HPTLC precoated plates, silica gel 60 F 254 from E. Merck, Darmstadt.

The mixing ratios of the mobile phases for all the chromatographic studies are always stated in volume/volume.

The term ether means diethyl ether.

Unless stated otherwise, petroleum ether with the boiling range of 50° C.–70° C. was used.

The compounds are numbered, and the figures in parentheses correspond to the number of the allocated compound.

Example 1

Z-3-[4-Dimethylaminomethyl-3-(3-methoxy-phenyl)-2-methyl-cyclohex-2-enylidenemethyl]-benzoic acid methyl ester hydrochloride (9) and E-3-[4-dimethylaminomethyl-3-(3-methoxy-phenyl)-2-methyl-cyclohex-2-enylidenemethyl]-benzoic acid methyl ester hydrochloride (10)

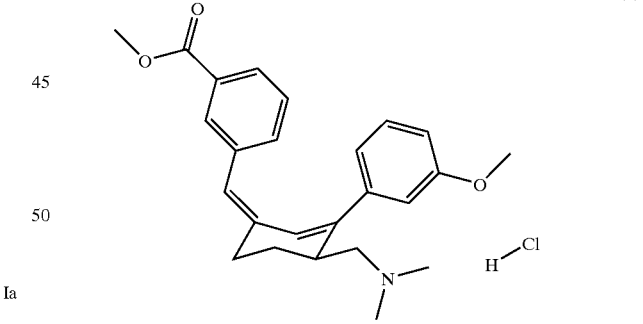

(9)

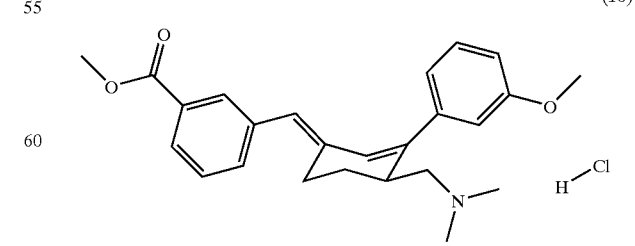

(10)

42.6 g potassium tert-butylate and 169.8 g 3-(benzoic acid methyl ester)-methyltriphenylphosphonium chloride were suspended in 1.51 analytical grade toluene under a nitrogen atmosphere at room temperature and the suspension was then stirred at 70° C. for one hour. 10 g 4-dimethylaminomethyl-3-(3-methoxy-phenyl)-cyclohex-2-enone in 100 ml analytical grade toluene were added at this temperature and the mixture was stirred at 70° C. for 3 days. The mixture was quenched with 500 ml water. The phases were separated and the aqueous phase was washed 3 times with 200 ml ethyl acetate each time. The combined organic phases were dried over magnesium sulfate and then freed from solvent in vacuo. The residue obtained in this way was taken up in a mixture of 150 ml ethyl acetate and 150 ml diiso-ether. The solid which had precipitated out was filtered off and washed with diiso-ether. The combined organic phases were freed from the solvent in vacuo. The residue was purified by column chromatography on silica gel with ethyl acetate/methanol=9/1. 5.3 g E-3-[4-dimethylaminomethyl-3-(3-methoxy-phenyl)-2-methyl-cyclohex-2-enylidenemethyl]-benzoic acid methyl ester were obtained as the first product fraction in the form of an orange-yellow oil. To prepare the hydrochloride, the oil was dissolved in 100 ml acetone, and an equimolar amount of trimethylchlorosilane and water was added. 5 g (30.7% of theory) of the title compound 10 were obtained in this way in the form of white crystals. 4 g Z-3-[4-dimethylaminomethyl-3-(3-methoxy-phenyl)-2-methyl-cyclohex-2-enylidenemethyl]-benzoic acid methyl ester were obtained as the second product fraction, likewise in the form of an orange-yellow oil. To liberate the hydrochloride, the oil was dissolved in 100 ml acetone, and an equimolar amount of trimethylchlorosilane and water was added. 3.5 g (21.5% of theory) of the title compound were obtained in this way in the form of white crystals.

Example 2 rac-trans-Z-3-[4-Dimethylaminomethyl-3-(3-methoxy-phenyl)-cyclohexylidenemethyl]-benzoic acid methyl ester hydrochloride (7) and rac-trans-E-3-[4-dimethylaminomethyl-3-(3-methoxy-phenyl)-cyclohexylidenemethyl]-benzoic acid methyl ester hydrochloride (8)

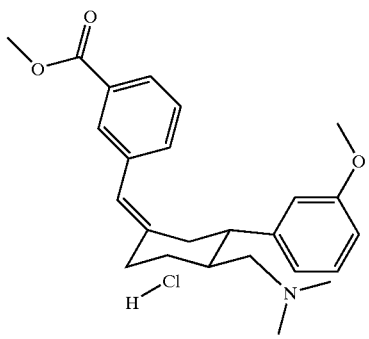

(7)

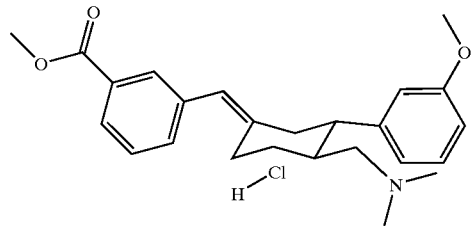

(8)

Employing:
rac-trans-4-dimethylaminomethyl-3-(3-methoxy-phenyl)-cyclohexanone instead of dimethylaminomethyl-3-(3-methoxy-phenyl)-cyclohex-2-enone in example 1, the procedure described in example 1 gave:
rac-trans-E-3-[4-dimethylaminomethyl-3-(3-methoxy-phenyl)-cyclohexylidenemethyl]-benzoic acid methyl ester hydrochloride (8), and
rac-trans-Z-3-[4-dimethylaminomethyl-3-(3-methoxy-phenyl)-cyclohexylidenemethyl]-benzoic acid methyl ester hydrochloride (7).

Example 3 rac-cis-Z-3-[4-Dimethylaminomethyl-3-(3-methoxy-phenyl)-cyclohexylidenemethyl]-benzoic acid methyl ester hydrochloride (6) and rac-cis-E-3-[4-dimethylaminomethyl-3-(3-methoxy-phenyl)-cyclohexylidenemethyl]-benzoic acid methyl ester; hydrochloride (5)

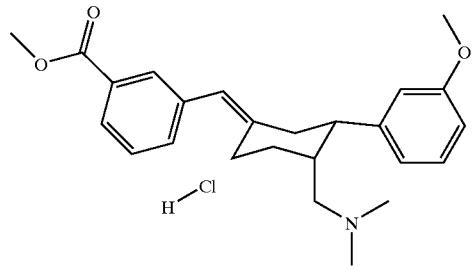

(5)

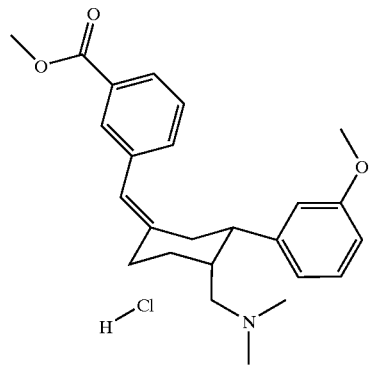

(6)

Employing rac-cis-4-dimethylaminomethyl-3-(3-methoxy-phenyl)-cyclohexanone instead of dimethylaminomethyl-3-(3-methoxy-phenyl)-cyclohex-2-enone in example 1, the procedure described in example 1 gave:
rac-cis-E-3-[4-dimethylaminomethyl-3-(3-methoxy-phenyl)-cyclohexylidenemethyl]-benzoic acid methyl ester hydrochloride (5), and rac-cis-Z-3-[4-dimethylaminomethyl-3-(3-methoxy-phenyl)-cyclohexylidenemethyl]-benzoic acid methyl ester hydrochloride (6).

Example 4

Z-3-[4-Dimethylaminomethyl-3-(3-methoxy-phenyl)-cyclohex-2-enylidenemethyl]-benzoic acid hydrochloride (14)

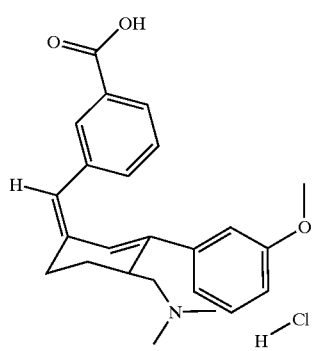

(14)

3 g of the Z-3-[4-dimethylaminomethyl-3-(3-methoxy-phenyl)-2-methyl-cyclohex-2-enylidenemethyl]-benzoic acid methyl ester, as the base, prepared according to example 1 were dissolved in 30 ml methanol, and 30 ml 1 N potassium hydroxide solution were added. The mixture was stirred at 60° C. for 2 hours. After the reaction mixture had cooled to room temperature, 1 N hydrochloric acid was added to the mixture until a pH of 4 was established. The phases were separated and the aqueous phase was washed 3 times with 20 ml ethyl acetate each time. The combined organic phases were dried over magnesium sulfate and freed from the solvent in vacuo. 2.7 g Z-3-[4-dimethylaminomethyl-3-(3-methoxy-phenyl)-cyclohex-2-enylidenemethyl]-benzoic acid base were obtained in this way in the form of an orange-yellow oil. To prepare the hydrochloride, the base was dissolved in 10 ml acetone, and an equimolar amount of trimethylchlorosilane and water was added. 2.4 g (77% of theory) Z-3-[4-dimethylaminomethyl-3-(3-methoxy-phenyl)-cyclohex-2-enylidenemethyl]-benzoic acid hydrochloride (14) were obtained in this way in the form of white crystals.

Example 5

E-3-[4-Dimethylaminomethyl-3-(3-methoxy-phenyl)-cyclohex-2-enylidenemethyl]-benzoic acid hydrochloride (15)

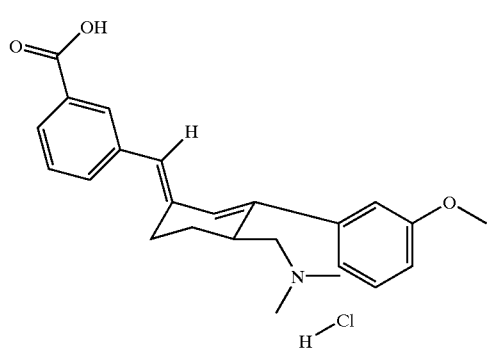

(15)

Employing:
E-3-[4-dimethylaminomethyl-3-(3-methoxy-phenyl)-2-methyl-cyclohex-2-enylidenemethyl]-benzoic acid methyl ester base, which was prepared according to example 1, instead of Z-3-[4-Dimethylaminomethyl-3-(3-methoxy-phenyl)-2-methyl-cyclohex-2-enylidenemethyl]-benzoic acid methyl ester base in example 4, the procedure described in example 4 gave E-3-[4-dimethylaminomethyl-3-(3-methoxy-phenyl)-cyclohex-2-enylidenemethyl]-benzoic acid hydrochloride (15).

Example 6 rac-trans-Z-3-[4-Dimethylaminomethyl-3-(3-methoxy-phenyl)-cyclohexylidenemethyl]-benzoic acid; hydrochloride (17)

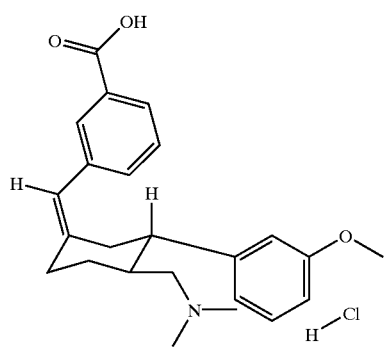

(17)

Employing:

rac-trans-Z-3-[4-dimethylaminomethyl-3-(3-methoxy-phenyl)-cyclohexylidenemethyl]-benzoic acid methyl ester base, which was prepared according to example 2, instead of Z-3-[4-Dimethylaminomethyl-3-(3-methoxy-phenyl)-2-methyl-cyclohex-2-enylidenemethyl]-benzoic acid methyl ester base in example 4, the procedure described in example 4 gave rac-trans-Z-3-[4-dimethylaminomethyl-3-(3-methoxy-phenyl)-cyclohexylidenemethyl]-benzoic acid hydrochloride (17).

Example 7 rac-trans-E-3-[4-Dimethylaminomethyl-3-(3-methoxy-phenyl)-cyclohexylidenemethyl]-benzoic acid hydrochloride (18)

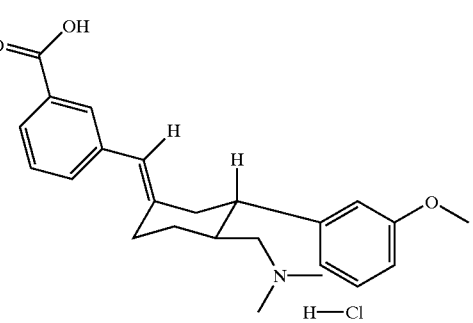

(18)

Employing
rac-trans-E-3-[4-dimethylaminomethyl-3-(3-methoxy-phenyl)-cyclohexylidenemethyl]-benzoic acid methyl ester base, which was prepared according to example 2,
  instead of Z-3-[4-dimethylaminomethyl-3-(3-methoxy-phenyl)-2-methyl-cyclohex-2-enylidenemethyl]-benzoic acid methyl ester base in example 4, the procedure described in example 4 gave rac-trans-E-3-[4-dimethylaminomethyl-3-(3-methoxy-phenyl)-cyclohexylidenemethyl]-benzoic acid hydrochloride (18).

Example 8 rac-cis-Z-3-[4-Dimethylaminomethyl-3-(3-methoxy-phenyl)-cyclohexylidenemethyl]-benzoic acid hydrochloride (27)

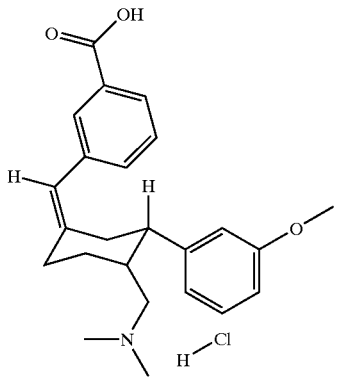

(27)

Employing
rac-cis-Z-3-[4-dimethylaminomethyl-3-(3-methoxy-phenyl)-cyclohexylidenemethyl]-benzoic acid methyl ester base, which was prepared according to example 3,
  instead of Z-3-[4-dimethylaminomethyl-3-(3-methoxy-phenyl)-2-methyl-cyclohex-2-enylidenemethyl]-benzoic acid methyl ester base in example 4, the procedure described in example 4 gave rac-cis-Z-3-[4-dimethylaminomethyl-3-(3-methoxy-phenyl)-cyclohexylidenemethyl]-benzoic acid hydrochloride (27).

Example 9 rac-cis-E-3-[4-Dimethylaminomethyl-3-(3-methoxy-phenyl)-cyclohexylidenemethyl]-benzoic acid hydrochloride (26)

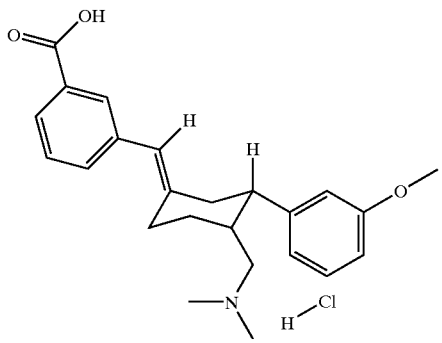

(26)

Employing:
rac-cis-E-3-[4-dimethylaminomethyl-3-(3-methoxy-phenyl)-cyclohexylidenemethyl]-benzoic acid methyl ester base, which was prepared according to example 3,
  instead of Z-3-[4-dimethylaminomethyl-3-(3-methoxy-phenyl)-2-methyl-cyclohex-2-enylidenemethyl]-benzoic acid methyl ester base in example 4, the procedure described in example 4 gave rac-cis-E-3-[4-dimethylaminomethyl-3-(3-methoxy-phenyl)-cyclohexylidenemethyl]-benzoic acid hydrochloride (26).

Example 10

Z-3-[4-Dimethylaminomethyl-3-(3-methoxy-phenyl)-cyclohex-2-enylidenemethyl]-N,N-diethyl-benzamide hydrochloride (34)

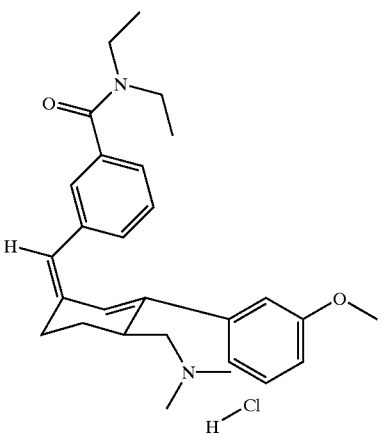

(34)

1.8 g of the Z-3-[4-dimethylaminomethyl-3-(3-methoxy-phenyl)-cyclohex-2-enylidenemethyl]-benzoic acid base prepared according to example 4 were dissolved in 50 ml analytical grade dimethylformamide, and 2 g DCC and 1.1 g hydroxysuccinimide were added at 0° C. to 15° C. The mixture was stirred at 0° C. for one hour and 2 ml diethylamine were then added dropwise at this temperature. The mixture was stirred at 0° C. for an additional hour and then at room temperature for four days. The reaction mixture was poured on to 300 ml saturated sodium chloride solution and the mixture was then extracted 3 times with 250 ml ethyl acetate each time. The organic phases were washed with 50 ml saturated sodium chloride solution and then dried over magnesium sulfate. The solvent was removed in vacuo. The residue was chromatographed on silica gel with ethyl acetate/methanol=6/5. 0.87 g Z-3-[4-dimethylaminomethyl-3-(3-methoxy-phenyl)-cyclohex-2-enylidenemethyl]-N,N-diethyl-benzamide base was obtained in this way in the form of an orange-yellow oil. To liberate the hydrochloride, the oil was dissolved in 5 ml acetone, and an equimolar amount of trimethylchlorosilane and water was added. 0.52 g (22.1% of theory) of the title compound 34 was obtained in this way in the form of white crystals.

Example 11

E-3-[4-Dimethylaminomethyl-3-(3-methoxy-phenyl)-cyclohex-2-enylidenemethyl]-N,N-diethyl-benzamide hydrochloride (31)

(31)

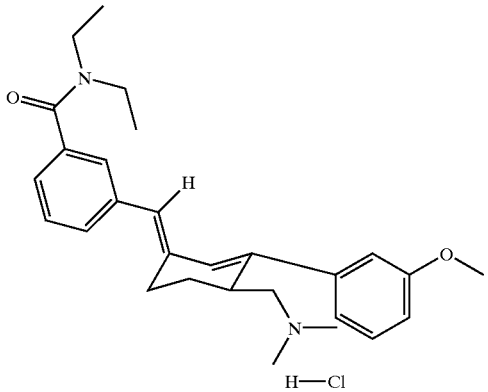

Employing:
E-3-[4-dimethylaminomethyl-3-(3-methoxy-phenyl)-cyclohex-2-enylidenemethyl]-benzoic acid as the base, which was prepared according to example 5,
  instead of Z-3-[4-dimethylaminomethyl-3-(3-methoxy-phenyl)-cyclohex-2-enylidenemethyl]-benzoic acid in example 10, the procedure described in example 10 gave E-3-[4-dimethylaminomethyl-3-(3-methoxy-phenyl)-cyclohex-2-enylidenemethyl]-N,N-diethyl-benzamide hydrochloride (31).

Example 12 rac-trans-Z-3-[4-Dimethylaminomethyl-3-(3-methoxy-phenyl)-cyclohexylidenemethyl]-N,N-diethyl-benzamide hydrochloride (36)

(36)

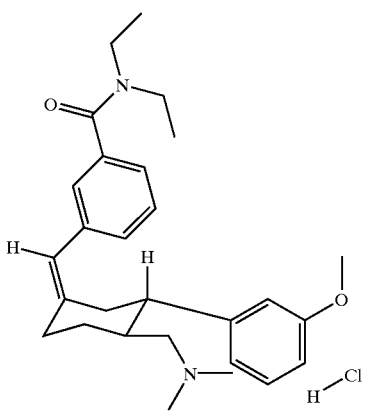

Employing:
rac-trans-Z-3-[4-dimethylaminomethyl-3-(3-methoxy-phenyl)-cyclohexylidenemethyl]-benzoic acid as the base, which was prepared according to example 6,
  instead of Z-3-[4-dimethylaminomethyl-3-(3-methoxy-phenyl)-cyclohex-2-enylidenemethyl]-benzoic acid in example 10, the procedure described in example 10 gave rac-trans-Z-3-[4-dimethylaminomethyl-3-(3-methoxy-phenyl)-cyclohexylidenemethyl]-N,N-diethyl-benzamide hydrochloride (36).

Example 13 rac-trans-E-3-[4-Dimethylaminomethyl-3-(3-methoxy-phenyl)-cyclohex-2-enylidenemethyl]-N,N-diethyl-benzamide hydrochloride (32)

(32)

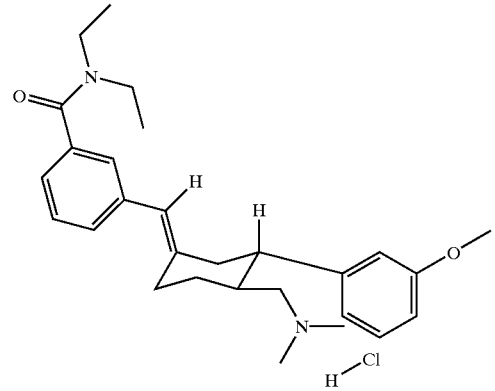

Employing:
rac-trans E-3-[4-dimethylaminomethyl-3-(3-methoxy-phenyl)-cyclohexylidenemethyl]-benzoic acid as the base, which was prepared according to example 7,
  instead of Z-3-[4-dimethylaminomethyl-3-(3-methoxy-phenyl)-cyclohex-2-enylidenemethyl]-benzoic acid in example 10, the procedure described in example 10 gave rac-trans-E-3-[4-dimethylaminomethyl-3-(3-methoxy-phenyl)-cyclohexylidenemethyl]-N,N-diethyl-benzamide hydrochloride (32).

Example 14 rac-cis-E-3-[4-Dimethylaminomethyl-3-(3-methoxy-phenyl)-cyclohexylidenemethyl]-N,N-diethyl-benzamide; hydrochloride (35)

(35)

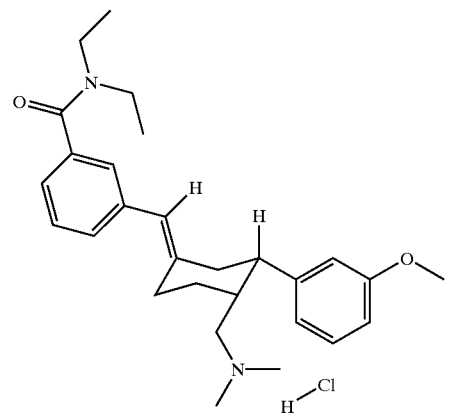

Employing:
rac-cis-E-3-[4-dimethylaminomethyl-3-(3-methoxy-phenyl)-cyclohexylidenemethyl]-benzoic acid as the base, which was prepared according to example 9,
  instead of Z-3-[4-dimethylaminomethyl-3-(3-methoxy-phenyl)-cyclohex-2-enylidenemethyl]-benzoic acid in example 10, the procedure described in example 10 gave rac-cis-E-3-[4-dimethylaminomethyl-3-(3-methoxy-phenyl)-cyclohexylidenemethyl]-N,N-diethyl-benzamide hydrochloride (35).

Example 15

Z-{3-[4-Dimethylaminomethyl-3-(3-methoxy-phenyl)-cyclohex-2-enylidenemethyl]-phenyl}-methanol; hydrochloride (25)

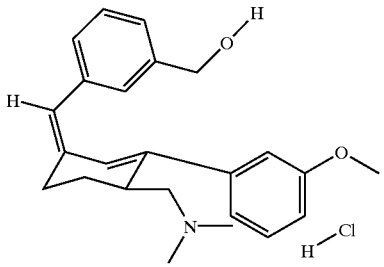

(25)

50 ml diisobutylaluminium hydride solution (25 wt. % soln. in toluene) were initially introduced into the reaction vessel under a nitrogen atmosphere. 1 g Z-3-[4-dimethylaminomethyl-3-(3-methoxy-phenyl)-2-methyl-cyclohex-2-enylidenemethyl]-benzoic acid methyl ester base, which was prepared according to example 1, dissolved in 100 ml analytical grade toluene, were then added dropwise at room temperature. The mixture was heated under reflux for two hours. When the reaction had ended the mixture was cooled to 0° C. and quenched with a mixture of 25 ml ethanol and 20 ml water. The precipitate which had precipitated out was filtered off with suction and washed with ethyl acetate. The organic phase was dried over magnesium sulfate and then freed from the solvent in vacuo. The residue was purified by column chromatography on silica gel with ethyl acetate/methanol=9/1. 580 mg of the title compound as the base were obtained in this way. To liberate the hydrochloride, the base was dissolved in 20 ml acetone, and an equimolar amount of trimethylchlorosilane and water was added. 550 mg (52.9% of theory) Z-(3-[4-dimethylaminomethyl-3-(3-methoxy-phenyl)-cyclohex-2-enylidenemethyl]-phenyl)-methanol; hydrochloride (25) were obtained in this way in the form of white crystals.

Example 16

E-{3-[4-Dimethylaminomethyl-3-(3-methoxy-phenyl)-cyclohex-2-enylidenemethyl]-phenyl]-methanol hydrochloride (16)

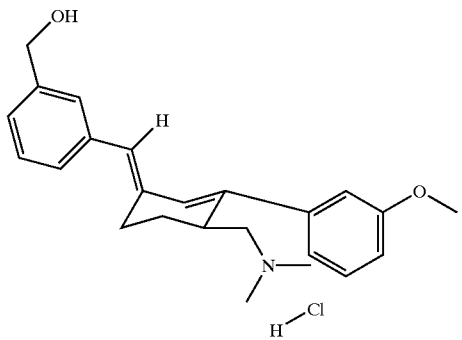

(16)

Employing:

E-3-[4-dimethylaminomethyl-3-(3-methoxy-phenyl)-2-methyl-cyclohex-2-enylidenemethyl]-benzoic acid methyl ester base, which was prepared according to example 1, instead of Z-3-[4-dimethylaminomethyl-3-(3-methoxy-phenyl)-2-methyl-cyclohex-2-enylidenemethyl]-benzoic acid methyl ester base in example 15, the procedure described in example 15 gave E-{3-[4-dimethylaminomethyl-3-(3-methoxy-phenyl)-cyclohex-2-enylidenemethyl]-phenyl}-methanol; hydrochloride (16).

Example 17

Z-3-[6-Dimethylaminomethyl-3-(3-hydroxymethyl-benzylidene)-cyclohex-1-enyl]-phenol; hydrochloride (40) and Z-3-[2-dimethylaminomethyl-5-(3-hydroxymethyl-benzylidene)-cyclohex-1-enyl]-phenol; hydrochloride (24)

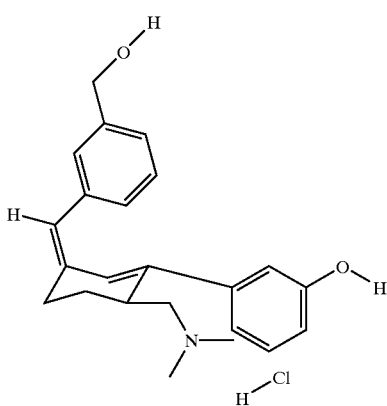

(40)

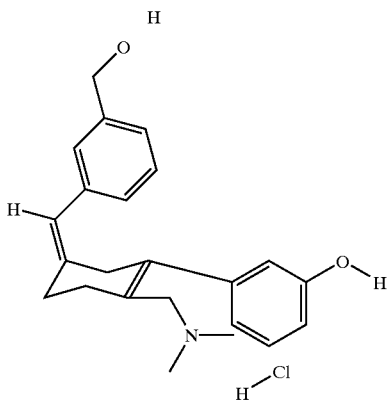

(24)

100 ml diisobutylaluminium hydride solution (25 wt. % soln. in toluene) were initially introduced into the reaction vessel under a nitrogen atmosphere. 1 g Z-3-[4-dimethylaminomethyl-3-(3-methoxy-phenyl)-2-methyl-cyclohex-2-enylidenemethyl]-benzoic acid methyl ester base, which was prepared according to example 1, dissolved in 100 ml analytical grade toluene, were then added dropwise at room temperature. The mixture was heated under reflux for six hours. When the reaction had ended the mixture was cooled to 0° C. and quenched with a mixture of 25 ml ethanol and 20 ml water. The precipitate which had precipitated out was filtered off with suction and washed with ethyl acetate. The organic phase was dried over magnesium sulfate and then freed from the solvent in vacuo. The residue was purified by column chromatography on silica gel with ethyl acetate/methanol=9/1. 200 mg Z-3-[2-dimethylaminomethyl-5-(3-hydroxymethyl-benzylidene)-cyclohex-1-enyl]-phenol base were obtained as the first product fraction. To liberate the hydrochloride, the base was dissolved in 20 ml acetone, and an equimolar amount of trimethylchlorosilane and water was added. 180 mg (17.9% of theory) Z-3 [2-dimethylaminomethyl-5-(3- hydroxymethyl-benzylidene)-cyclohex-1-enyl]-phenol; hydrochloride (24) were obtained in this way in the form of white crystals. 440 mg Z-3-[6-dimethylaminomethyl-3-(3-hydroxymethyl-benzylidene)-cyclohex-1-enyl]-phenol base were obtained as the second product fraction. To liberate the hydrochloride, the base was dissolved in 20 ml acetone, an equimolar amount of trimethylchlorosilane and water was added and 410 mg (40.9% of theory) Z-3-[6-Dimethylaminomethyl-3-(3-hydroxymethyl-benzylidene)-cyclohex-1-enyl]-phenol; hydrochloride (40) were obtained in this way in the form of white crystals.

Example 18

E-3-[6-Dimethylaminomethyl-3-(3-hydroxymethyl-benzylidene)-cyclohex-1-enyl]-phenol; hydrochloride (22)

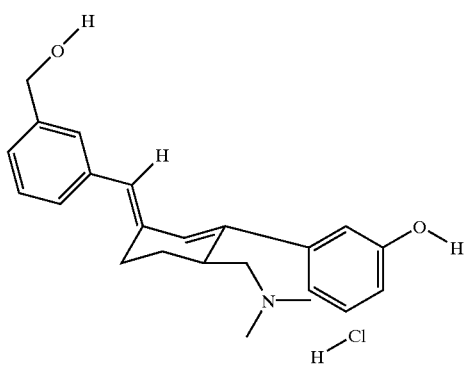

(22)

Employing:
E-3-[4-dimethylaminomethyl-3-(3-methoxy-phenyl)-2-methyl-cyclohex-2-enylidenemethyl]-benzoic acid methyl ester base, which was prepared according to example 1,
instead of Z-3-[4-dimethylaminomethyl-3-(3-methoxy-phenyl)-2-methyl-cyclohex-2-enylidenemethyl]-benzoic acid methyl ester base in example 17, the procedure described in example 17 gave exclusively E-3-[6-dimethylaminomethyl-3-(3-hydroxymethyl-benzylidene)-cyclohex-1-enyl]-phenol; hydrochloride (22).

Example 19 rac-trans-E-[3-(2-Dimethylaminomethyl-5-(3-hydroxymethyl-benzylidene)-cyclohexyl)-phenol, hydrochloride (19)

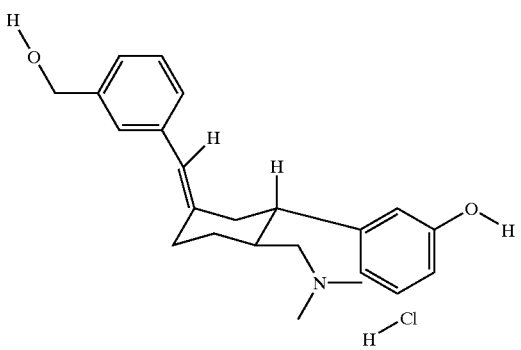

(19)

Employing:

rac-trans-E-3-[4-dimethylaminomethyl-3-(3-methoxy-phenyl)-cyclohexylidenemethyl]-benzoic acid methyl ester base, which was prepared according to example 2, instead of Z-3-[4-dimethylaminomethyl-3-(3-methoxy-phenyl)-2-methyl-cyclohex-2-enylidenemethyl]-benzoic acid methyl ester base in example 17, the procedure described in example 17 gave exclusively rac-trans-E-3-[2-dimethylaminomethyl-5-(3-hydroxymethyl-benzylidene)-cyclohexyl]-phenol hydrochloride (19).

Example 20

Z-3-[4-Dimethylaminomethyl-3-(3-methoxy-phenyl)-2-methyl-cyclohex-2-enylidenemethyl]-naphthalene-1-carboxylic acid ethyl ester; hydrochloride (11) and E-3-[4-dimethylaminomethyl-3-(methoxy-phenyl)-2-methyl-cyclohex-2-enylidenemethyl]-naphthalene-1-carboxylic acid ethyl ester hydrochloride (12)

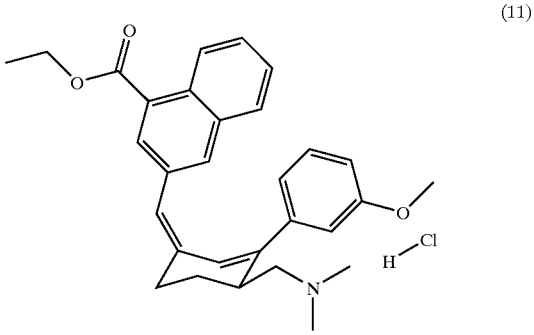

(11)

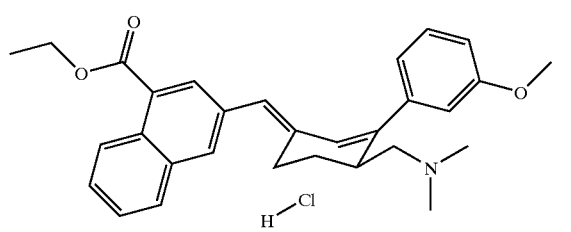

(12)

Employing:

3-(naphthyl-1-carboxylic acid ethyl ester)-methyl-triphenylphosphonium chloride instead of 3-(benzoic acid methyl ester)-methyltriphenylphosphonium chloride in example 1, the procedure described in example 1 gave
Z-3-[4-dimethylaminomethyl-3-(3-methoxy-phenyl)-2-methyl-cyclohex-2-enylidenemethyl]-naphthalene-1-carboxylic acid ethyl ester; hydrochloride (11) and E-3-[4-dimethylaminomethyl-3-(3-methoxy-phenyl)-2-methyl-cyclohex-2-enylidenemethyl]-naphthalene-1-carboxylic acid ethyl ester hydrochloride (12).

Example 21

Z-3-[4-Dimethylaminomethyl-3-(3-methoxy-phenyl)-cyclohexylidenemethyl]-2-fluoro-benzoic acid ethyl ester hydrochloride (13)

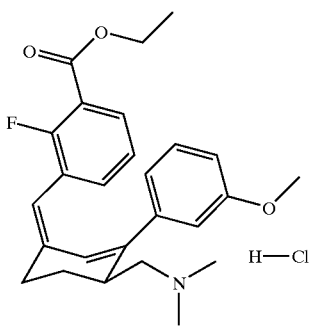

(13)

Employing:

(2-fluoro-3-benzoic acid ethyl ester)-methyl-triphenylphosphonium chloride instead of 3-(benzoic acid methyl ester)-methyltriphenylphosphonium chloride in example 1, the procedure described in example 1 gave exclusively Z-3-[4-dimethylaminomethyl-3-(3-methoxy-phenyl)-cyclohexylidenemethyl]-2-fluoro-benzoic acid ethyl ester hydrochloride (13).

Example 22

E-3-[4-Dimethylaminomethyl-3-(3-methoxy-phenyl)-cyclohex-2-enylidenemethyl]-benzoic acid tert-butyl ester; hydrochloride (21)

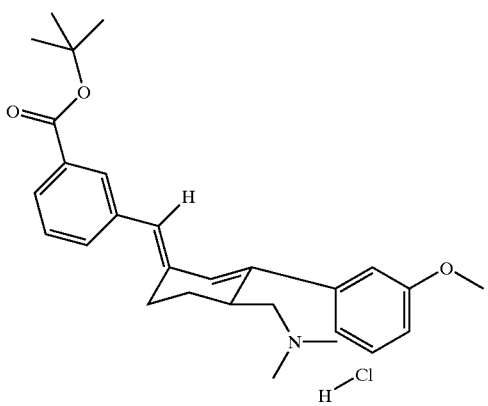

(21)

Employing:

(3-benzoic acid tert-butyl ester)-methyl-triphenylphosphonium chloride)

instead of 3-(benzoic acid methyl ester)-methyltriphenylphosphonium chloride in example 1, the procedure described in example 1 gave exclusively E-3-[4-dimethylaminomethyl-3-(3-methoxy-phenyl)-cyclohex-2-enylidenemethyl]-benzoic acid tert-butyl ester; hydrochloride (21).

Example 23

E-3-[4-Dimethylaminomethyl-3-(3-methoxy-phenyl)-cyclohex-2-enylidenemethyl]-benzoic acid ethyl ester; hydrochloride (33)

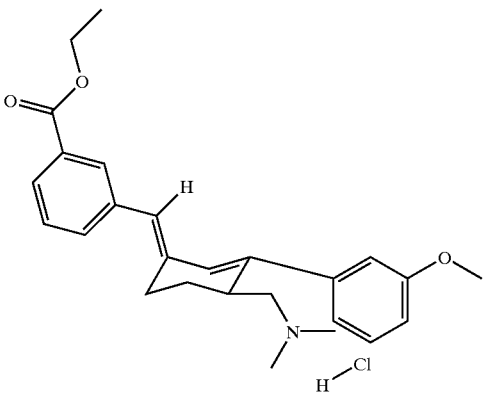

(33)

Employing:

(3-benzoic acid ethyl ester)-methyltriphenylphosphonium chloride instead of 3-(benzoic acid methyl ester)-methyltriphenylphosphonium chloride in example 1, the procedure described in example 1 gave exclusively E-3-[4-dimethylaminomethyl-3-(3-methoxy-phenyl)-cyclohex-2-enylidenemethyl]-benzoic acid ethyl ester; hydrochloride (33).

Example 24

Z-3-[4-Dimethylaminomethyl-3-(3-methoxy-phenyl)-cyclohex-2-enylidenemethyl]-benzoic acid isobutyl ester; hydrochloride (39)

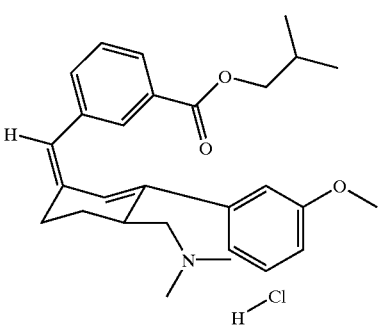

(39)

Employing:

(3-benzoic acid isobutyl ester)-methyl-triphenylphosphonium chloride instead of 3-(benzoic acid methyl ester)-methyltriphenylphosphonium chloride in example 1, the procedure described in example 1 gave exclusively Z-3-[4-dimethylaminomethyl-3-(3-methoxy-phenyl)-cyclohex-2-enylidenemethyl]-benzoic acid isobutyl ester; hydrochloride (39).

Example 25 rac-trans-E-3-[4-Dimethylaminomethyl-3-(3-methoxy-phenyl)-cyclohexylidenemethyl]-benzoic acid tert-butyl ester; hydrochloride (28)

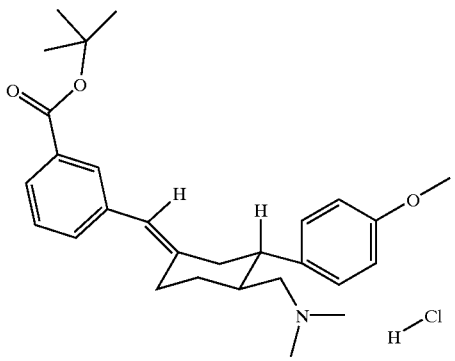

(28)

Employing:

(3-benzoic acid tert-butyl ester)-methyl-triphenylphosphonium chloride instead of 3-(benzoic acid methyl ester)-methyltriphenylphosphonium chloride in example 2, the procedure described in example 2 gave exclusively rac-trans-E-3-[4-dimethylaminomethyl-3-(3-methoxy-phenyl)-cyclohexylidenemethyl]-benzoic acid tert-butyl ester; hydrochloride (28).

Example 26 rac-cis-Z-3-[4-Dimethylaminomethyl-3-(3-methoxy-phenyl)-cyclohexylidenemethyl]-benzoic acid ethyl ester; hydrochloride (30)

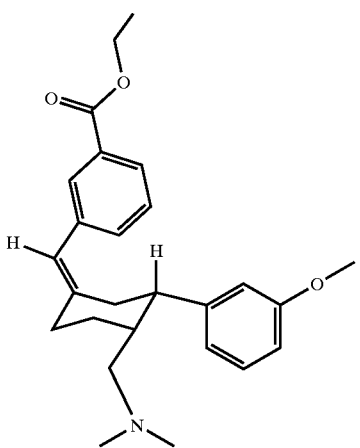

(30)

Employing:

(3-benzoic acid ethyl ester)-methyl-triphenylphosphonium chloride instead of 3-(benzoic acid methyl ester)-methyltriphenylphosphonium chloride in example 3, the procedure described in example 3 gave exclusively rac-cis-Z-3-[4-dimethylaminomethyl-3-(3-methoxy-phenyl)-cyclohexylidenemethyl]-benzoic acid ethyl ester; hydrochloride (30).

Example 27

Z-[4-(4–Chloro-benzylidene)-2-(3-methoxy-phenyl)-cyclohex-2-enylmethyl]-dimethyl-amine; hydrochloride (41) and E-[4-(4-chloro-benzylidene)-2-(3-methoxy-phenyl)-cyclohex-2-enylmethyl]-dimethyl-amine; hydrochloride (46)

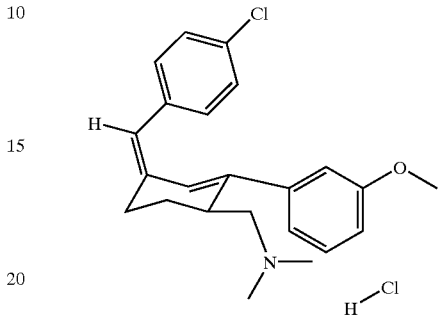

(41)

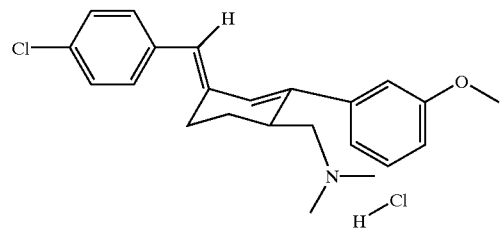

(46)

21.6 g potassium tert-butylate and 65 g 4-chlorobenzyltriphenylphosphonium chloride were suspended in 800 ml analytical grade toluene under a nitrogen atmosphere at room temperature and the suspension was then stirred at 70° C. for one hour. 11.5 g 4-dimethylaminomethyl-3-(3-methoxy-phenyl)-cyclohex-2-enone in 100 ml analytical grade toluene were added at this temperature and the mixture was stirred at 70° C. for 3 days. The mixture was quenched with 500 ml water. The phases were separated and the aqueous phase was washed 3 times with 200 ml ethyl acetate each time. The combined organic phases were dried over magnesium sulfate and then freed from the solvent in vacuo. The solid which had precipitated out was filtered off and washed with diiso-ether. The combined organic phases were freed from the solvent in vacuo. The residue was purified by column chromatography on silica gel with ethyl acetate/methanol=9/1. 5.2 g E-[4-(4-chloro-benzylidene)-2-(3-methoxy-phenyl)-cyclohex-2-enylmethyl]-dimethyl-amine base were obtained as the first product fraction. To prepare the hydrochloride, the base was dissolved in 50 ml acetone, and an equimolar amount of trimethylchlorosilane and water was added. 4.7 g (27.6% of theory) of the title compound 46 were obtained in this way in the form of white crystals. 3.5 g Z-[4-(4-chloro-benzylidene)-2-(3-methoxy-phenyl)-cyclohex-2-enylmethyl]-dimethyl-amine base were obtained as the second product fraction. To liberate the hydrochloride, the base was dissolved in 50 ml acetone, and an equimolar amount of trimethylchlorosilane and water was added. 3 g (17.6% of theory) of the title compound 41 were obtained in this way in the form of white crystals.

Example 28

E-3-[3-(4–Chloro-benzylidene)-6-dimethylaminomethyl-cyclohex-1-enyl]-phenol; hydrochloride (47)

(47)

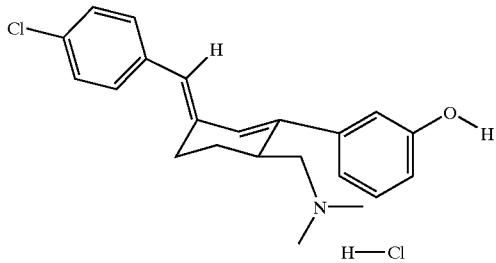

850 mg E-[4-(4-chloro-benzylidene)-2-(3-methoxy-phenyl)-cyclohex-2-enylmethyl]-dimethyl-amine base, which was prepared according to example 27, dissolved in 50 ml analytical grade toluene, were added to 50 ml diisobutylaluminium hydride solution (25 wt. % soln. in toluene). The mixture was heated under reflux for 8 hours. The reaction solution was subsequently quenched with 100 ml ethanol and then with 100 ml water. The precipitate which had precipitated out was filtered off with suction and washed with toluene. The combined organic phases were dried over magnesium sulfate and the solvent was then evaporated in vacuo. The residue was purified on silica gel with ethyl acetate/methanol=9/1. 500 mg of the title compound 47 as the base were obtained in this way. To liberate the hydrochloride, the title compound was dissolved in 50 ml acetone, and an equimolar amount of trimethylchlorosilane and water was added. 430 mg (52.5% of theory) E-3-[3-(4-chloro-benzylidene)-6-dimethylaminomethyl-cyclohex-1-enyl]-phenol; hydrochloride (47) were obtained in this way in the form of white crystals.

Example 29

Z-[4-(4-Fluoro-benzylidene)-2-(3-methoxy-phenyl)-cyclohex-2-enylmethyl]-dimethyl-amine; hydrochloride (43) and E-[4-(4-fluoro-benzylidene)-2-(3-methoxy-phenyl)-cyclohex-2-enylmethyl]-dimethyl-amine; hydrochloride (42)

(42)

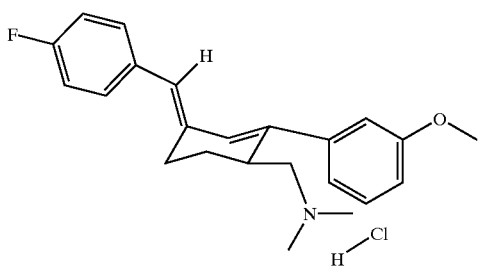

(43)

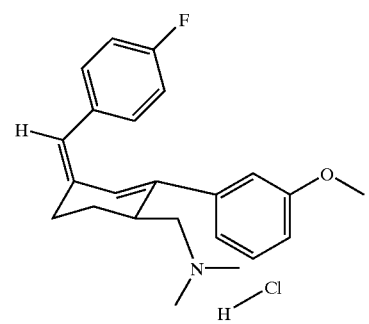

21.6 g potassium tert-butylate and 70 g 4-fluorobenzyltriphenylphosphonium chloride were suspended in 800 ml analytical grade toluene under a nitrogen atmosphere at room temperature and the suspension was then stirred at 70° C. for one hour. 11.5 g 4-dimethylaminomethyl-3-(3-methoxy-phenyl)-cyclohex-2-enone in 100 ml analytical grade toluene were added at this temperature and the mixture was stirred at 70° C. for 3 days. The mixture was quenched with 500 ml water. The phases were separated and the aqueous phase was washed 3 times with 200 ml ethyl acetate each time. The combined organic phases were dried over magnesium sulfate and then freed from the solvent in vacuo. The solid which had precipitated out was filtered off and washed with diiso-ether. The combined organic phases were freed from the solvent in vacuo. The residue was purified by column chromatography on silica gel with ethyl acetate/methanol=9/1. 5.4 g E-[4-(4-fluoro-benzylidene)-2-(3-methoxy-phenyl)-cyclohex-2-enylmethyl]-dimethyl-amide were obtained as the first product fraction. To prepare the hydrochloride, the base was dissolved in 50 ml acetone, and an equimolar amount of trimethylchlorosilane and water was added. 5.1 g (30% of theory) of the title compound 42 were obtained in this way in the form of white crystals. 4.2 g Z-[4-(4-fluoro-benzylidene)-2-(3-methoxy-phenyl)-cyclohex-2-enylmethyl]-dimethyl-amine were obtained as the second product fraction. To liberate the hydrochloride, the base was dissolved in 50 ml acetone, and an equimolar amount of water and trimethylchlorosilane was added. 3.9 g (22.9% of theory) of the title compound 43 were obtained in this way in the form of white crystals.

Example 30

Z-3-[6-Dimethylaminomethyl-3-(4-fluoro-benzylidene)-cyclohex-1-enyl]-phenol; hydrochloride (45)

(45)

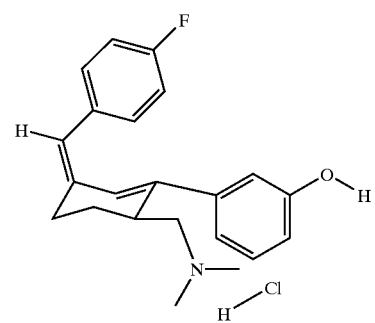

Employing:

Z-[4-(4-fluoro-benzylidene)-2-(3-methoxy-phenyl)-cyclohex-2-enylmethyl]-dimethyl-amine base instead of E-[4-(4-chloro-benzylidene)-2-(3-methoxy-phenyl)-cyclohex-2-enylmethyl]-dimethyl-amine base in example 28, the procedure described in example 28 gave Z-3-[6-dimethylaminomethyl-3-(4-fluoro-benzylidene)-cyclohex-1-enyl]-phenol; hydrochloride (45).

Example 31

E-3-[6-Dimethylaminomethyl-3-(4-fluoro-benzylidene)-cyclohex-1-enyl]-phenol; hydrochloride (44)

(44)

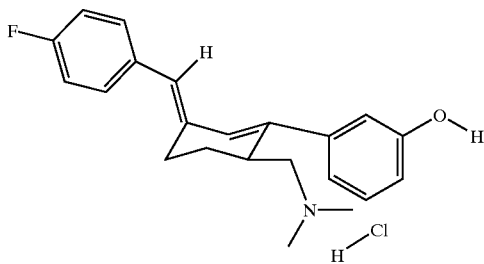

Employing:

E-[4-(4-fluoro-benzylidene)-2-(3-methoxy-phenyl)-cyclohex-2-enylmethyl]-dimethyl-amine base instead of E-[4-(4-chloro-benzylidene)-2-(3-methoxy-phenyl)-cyclohex-2-enylmethyl]-dimethyl-amine base in example 28, the procedure described in example 28 gave E-3-[6-dimethylaminomethyl-3-(4-fluoro-benzylidene)-cyclohex-1-enyl]-phenol; hydrochloride (44).

Example 32

Z-3-[4-Dimethylaminomethyl-3-(3-hydroxy-phenyl)-cyclohex-2-enylidenemethyl]-benzoic acid methyl ester hydrochloride (38) and E-3-[4-dimethylaminomethyl-3-(3-hydroxy-phenyl)-cyclohex-2-enylidenemethyl]-benzoic acid methyl ester hydrochloride (37)

(37)

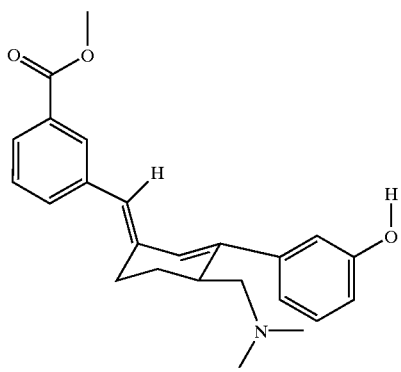

(38)

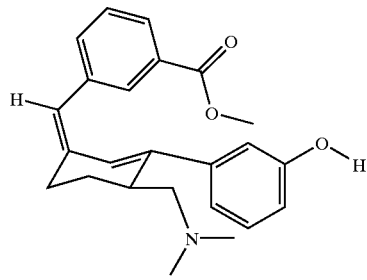

8.1 g potassium tert-butylate and 35.4 g 3-(benzoic acid methyl ester)-methyltriphenylphosphonium chloride were suspended in 800 ml analytical grade toluene under a nitrogen atmosphere at room temperature and the suspension was then stirred at 70° C. for one hour. 7 g 3-(3-(tert-butyl-diphenyl-silanyloxy)-cyclohex-2-enone in 100 ml analytical grade toluene were added at this temperature and the mixture was stirred at 70° C. for 3 days. The mixture was quenched with 500 ml water. The phases were separated and the aqueous phase was washed 3 times with 200 ml ethyl acetate each time. The combined organic phases were dried over magnesium sulfate and then freed from solvent in vacuo. The residue obtained in this way was taken up in a mixture of 150 ml ethyl acetate and 150 ml diiso-ether. The solid which had precipitated out was filtered off and washed with diiso-ether. The combined organic phases were freed from the solvent in vacuo. The residue (16.7 g) was dissolved in 70 ml tetrahydrofuran, and 16.7 ml tetrabutylammonium fluoride were added. After a reaction time of 10 minutes the reaction solution was quenched with 50 ml water and extracted three times with 50 ml ethyl acetate each time. The combined organic phases were dried over magnesium sulfate and then freed from the solvent in vacuo. The residue was purified by column chromatography on silica gel with ethyl acetate/methanol=9/1. 2.5 g E-3-[4-dimethylaminomethyl-3-(3-hydroxy-phenyl)-cyclohex-2-enylidenemethyl]-benzoic acid methyl ester base were obtained as the first product fraction. To liberate the hydrochloride, the base was dissolved in 50 ml acetone, and an equimolar amount of trimethylchlorosilane and water was added. 2 g (36.8% of theory) E-3-[4-dimethylaminomethyl-3-(3-hydroxy-phenyl)-cyclohex-2-enylidenemethyl]-benzoic acid methyl ester hydrochloride (37) were obtained in this way. 1.8 g (27.6% of theory) Z-3[4-Dimethylaminomethyl-3-(3-hydroxy-phenyl)-cyclohex-2-enylidenemethyl]-benzoic acid methyl ester were obtained as the second product fraction. To liberate the hydrochloride, the base was dissolved in 50 ml acetone, and an equimolar amount of trimethylchlorosilane and water was added. 1.5 g (27.6% of theory) Z-3-[4-dimethylaminomethyl-3-(3-hydroxy-phenyl)-cyclohex-2-enylidenemethyl]-benzoic acid methyl ester hydrochloride (38) were obtained in this way.

Example 33 rac-cis-Z-3-[4-Dimethylaminomethyl-3-(3-hydroxy-phenyl)-cyclohexylidenmethyl]-benzoic acid methyl ester; hydrochloride (51) and rac-cis-E-3-[4-dimethylaminomethyl-3-(3-hydroxy-phenyl)-cyclohexylidenmethyl]-benzoic acid methyl ester; hydrochloride (50)

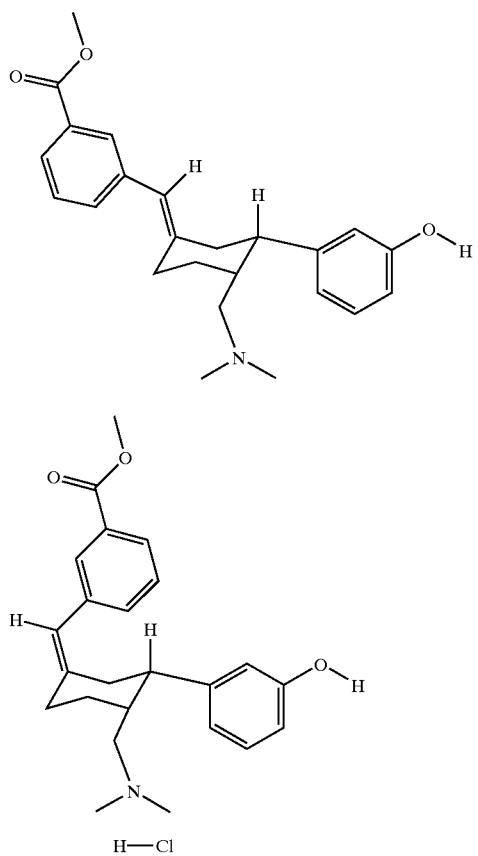

Employing:

rac-cis-3-(3-(tert-butyl-diphenyl-silanyloxy)-phenyl)-cyclohexanone instead of 3-(3-(tert-butyl-diphenyl-silanyloxy)-cyclohex-2-enone in example 32, the procedure described in example 32 gave rac-cis-Z-3-[4-dimethylaminomethyl-3-(3-hydroxy-phenyl)-cyclohexylidenmethyl]-benzoic acid methyl ester; hydrochloride (51) and rac-cis-E-3-[4-dimethylaminomethyl-3-(3-hydroxy-phenyl)-cyclohexylidenmethyl]-benzoic acid methyl ester; hydrochloride (50).

Example 34

Z-3-[4-Dimethylaminomethyl-3-(3-hydroxy-phenyl)-cyclohex-2-enylidenemethyl]-benzoic acid hydrochloride (48)

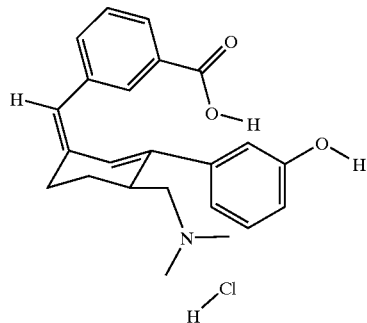

3 g of the Z-3-[4-Dimethylaminomethyl-3-(3-hydroxy-phenyl)-cyclohex-2-enylidenmethyl]-benzoic acid methyl ester, as the base, prepared according to example 32 were dissolved in 30 ml methanol, and 30 ml 1 N potassium hydroxide solution were added. The mixture was stirred at 60° C. for 2 hours. After the reaction mixture had cooled to room temperature, 1 N hydrochloric acid was added to the mixture until a pH of 4 was established. The phases were separated and the aqueous phase was washed 3 times with 20 ml ethyl acetate each time. The combined organic phases were dried over magnesium sulfate and freed from the solvent in vacuo. Z-3-[4-Dimethylaminomethyl-3-(3-hydroxy-phenyl)-cyclohex-2-enylidenmethyl]-benzoic acid, 2.7 g in the form of an orange-yellow oil, was obtained in this way. To prepare the hydrochloride, the base was dissolved in 10 ml acetone, and an equimolar amount of trimethylchlorosilane and water was added. 2.4 g (77.7% of theory) Z-3-[4-dimethylaminomethyl-3-(3-hydroxy-phenyl)-cyclohex-2-enylidenmethyl]-benzoic acid hydrochloride were obtained in this way.

Example 35

E-3-[4-Dimethylaminomethyl-3-(3-hydroxy-phenyl)-cyclohex-2-enylidenemethyl]-benzoic acid; hydrochloride (49)

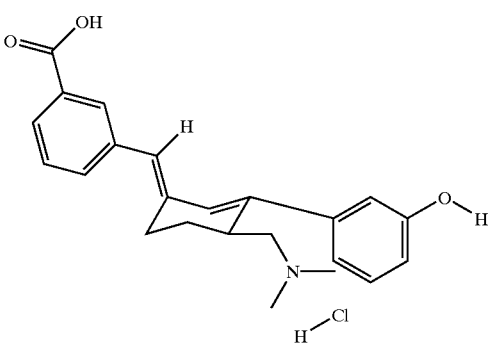

Employing:
E-3-[4-dimethylaminomethyl-3-(3-hydroxy-phenyl)-cyclohex-2-enylidenemethyl]-benzoic acid methyl ester as the base, which was prepared according to example 32,
instead of Z-3-[4-dimethylaminomethyl-3-(3-hydroxy-phenyl)-cyclohex-2-enylidenemethyl]-benzoic acid methyl ester base in example 34, the procedure described in example 34 gave E-3-[4-dimethylaminomethyl-3-(3-hydroxy-phenyl)-cyclohex-2-enylidenemethyl]-benzoic acid; hydrochloride (49).

Example 36 rac-trans-Z-3-[4-Dimethylaminomethyl-3-(3-hydroxy-phenyl)-cyclohexylidenemethyl]-benzoic acid; hydrochloride (52)

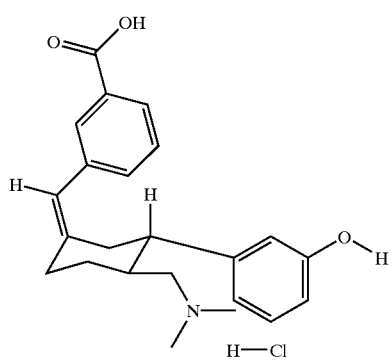

(52)

Employing:

rac-trans-Z-3-[4-dimethylaminomethyl-3-(3-hydroxy-phenyl)-cyclohex-2-enylidenemethyl]-benzoic acid methyl ester as the base
  instead of Z-3-[4-dimethylaminomethyl-3-(3-hydroxy-phenyl)-cyclohex-2-enylidenemethyl]-benzoic acid methyl ester base in example 34, the procedure described in example 34 gave rac-trans-Z-3-[4-dimethylaminomethyl-3-(3-hydroxy-phenyl)-cyclohexylidenemethyl]-benzoic acid; hydrochloride (52).

Example 37 rac-trans-E-3-[4-Dimethylaminomethyl-3-(3-hydroxy-phenyl)-cyclohexylidenemethyl]-benzoic acid hydrochloride (53)

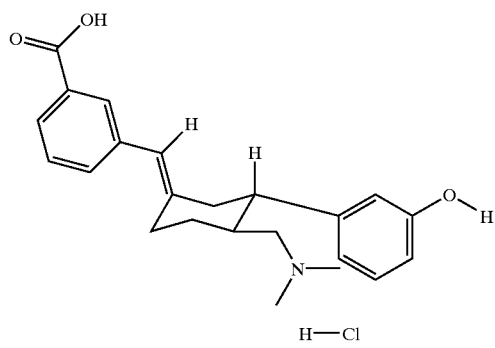

(53)

Employing:

rac-trans-E-3-[4-dimethylaminomethyl-3-(3-hydroxy-phenyl)-cyclohex-2-enylidenemethyl]-benzoic acid methyl ester as the base
  instead of Z-3-[4-dimethylaminomethyl-3-(3-hydroxy-phenyl)-cyclohex-2-enylidenemethyl]-benzoic acid methyl ester base in example 34, the procedure described in example 34 gave rac-trans-E-3-[4-dimethylaminomethyl-3-(3-hydroxy-phenyl)-cyclohexylidenemethyl]-benzoic acid; hydrochloride (53).

Example 38 rac-trans-Z-[4-Benzylidene-2-(3-methoxy-phenyl)-cyclohexylmethyl]-dimethylamine hydrochloride (3) and rac-trans-E-[4-benzylidene-2-(3-methoxy-phenyl)-cyclohexylmethyl]-dimethylamine hydrochloride (2)

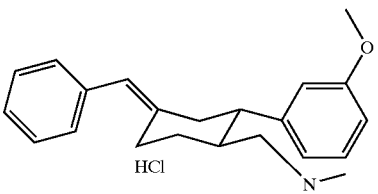

(2)

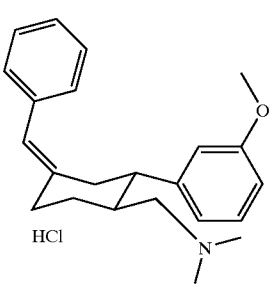

(3)

Employing:

rac-trans-4-dimethylaminomethyl-3-(3-methoxy-phenyl)-cyclohexanone instead of dimethylaminomethyl-3-(3-methoxy-phenyl)-cyclohex-2-enone in example 1
  and benzyltriphenylphosphonium chloride instead of 3-(benzoic acid methyl ester)-methyltriphenylphosphonium chloride in example 1
  the procedure described in example 1 gave:
    rac-trans-Z-[4-benzylidene-2-(3-methoxy-phenyl)-cyclohexylmethyl]-dimethylamine hydrochloride (3) and rac-trans-E-[4-benzylidene-2-(3-methoxy-phenyl)-cyclohexylmethyl]-dimethylamine hydrochloride (2).

Example 39 rac-trans-Z-3-(5-Benzylidene-2-dimethylaminomethyl-cyclohexyl)-phenol; hydrochloride (23)

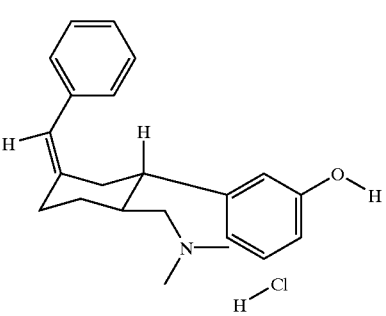

(23)

140 ml diisobutylaluminium hydride solution (25 wt. % soln. in toluene) were initially introduced into the reaction vessel under a nitrogen atmosphere. 2.4 g rac-trans-Z-[4-benzylidene-2-(3-methoxy-phenyl)-cyclohexylmethyl}-dimethylamine base, which was prepared according to example 39, dissolved in 20 ml analytical grade toluene, were then added dropwise at room temperature. The mixture was heated under reflux for two hours, When the reaction had ended the mixture was cooled to 0° C. and quenched with a mixture of 25 ml ethanol and 20 ml water. The precipitate which had precipitated out was filtered off with suction and washed with ethyl acetate. The organic phase was dried over magnesium sulfate and then freed from the solvent in vacuo. The residue was purified by column chromatography on silica gel with ethyl acetate/methanol= 9/1. 1 g of the title compound as the base was obtained in this way. To liberate the hydrochloride, the base was dissolved in 20 ml acetone, and an equimolar amount of trimethylchlorosilane and water was added. 300 mg (17.1% of theory) rac-trans-Z-3-(5-benzylidene-2-dimethylaminomethyl-cyclohexyl)-phenol; hydrochloride (23) was obtained in this way in the form of white crystals.

Example 40 rac-trans-E-3-[5-Benzylidene-2-dimethylaminomethyl-cyclohexyl)-phenol; hydrochloride (20)

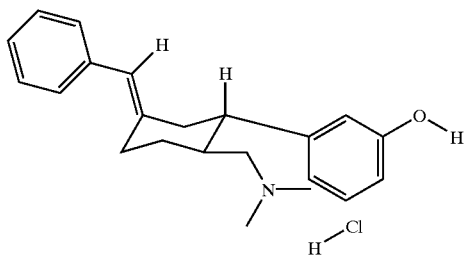

(20)

Employing:

rac-trans-E-[4-benzylidene-2-(3-methoxy-phenyl)-cyclohexylmethyl]-dimethylamine base instead of rac-trans-Z-[4-benzylidene-2-(3-methoxy-phenyl)-cyclohexylmethyl]-dimethylamine base in example 39, the procedure described in example 39 gave rac-trans-E-3-(5-benzylidene-2-dimethylaminomethyl-cyclohexyl)-phenol; hydrochloride (20).

Example 41 rac-cis-Z-[-4-Benzylidene-2-(3-methoxy-phenyl)-cyclohexylmethyl]-dimethylamine hydrochloride (4) and rac-cis-E-[4-benzylidene-2-(3-methoxy-phenyl)-cyclohexylmethyl]-dimethylamine hydrochloride (1)

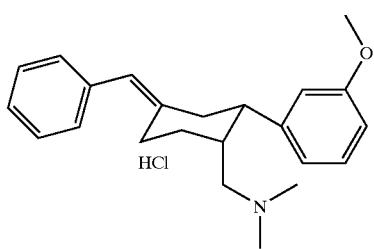

(1)

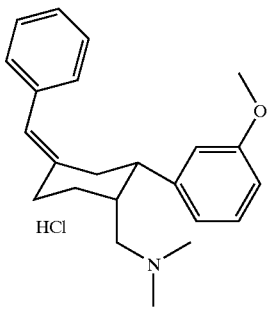

(4)

Employing:

rac-cis-4-dimethylaminomethyl-3-(3-methoxy-phenyl)-cyclohexanone instead of dimethylaminomethyl-3-(3-methoxy-phenyl)-cyclohex-2-enone in example 1 and benzyltriphenylphosphonium chloride instead of 3-(benzoic acid methyl ester)-methyltriphenylphosphonium chloride in example 1 the procedure described in example 1 gave
rac-cis-Z-[4-benzylidene-2-(3-methoxy-phenyl)-cyclohexylmethyl]-dimethylamine hydrochloride (4) and rac-cis-E-[-4-Benzylidene-2-(3-methoxy-phenyl)-cyclohexylmethyl]-dimethylamine hydrochloride (1).

Example 42 rac-trans-E-[3-[4-Dimethylaminomethyl-3-(3-methoxy-phenyl)-cyclohexylidenemethyl)-phenyl)-methanol]; hydrochloride (29)

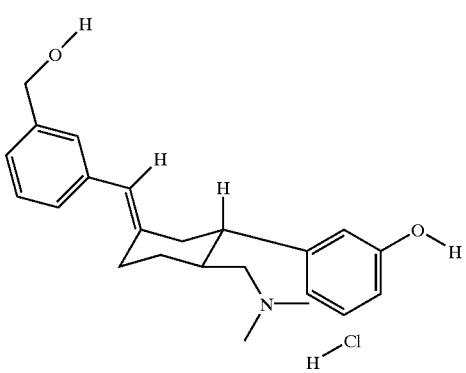

(29)

Employing rac-trans-E-3-[4-dimethylaminomethyl-3-(3-methoxy-phenyl)-cyclohexylidenemethyl]-benzoic acid methyl ester, which was prepared according to example 2, instead of Z-3-[4-dimethylaminomethyl-3-(3-methoxy-phenyl)-2-methyl-cyclohex-2-enylidenemethyl]-benzoic acid methyl ester in example 15, the procedure described in example 15 gave rac-trans-E-[3-[4-dimethylaminomethyl-3-(3-methoxy-phenyl)-cyclohexylidenemethyl)-phenyl)-methanol]; hydrochloride (29).

Example 43

The following compounds were prepared in accordance with the instructions described above. The particular structure is demonstrated by NMR:

rac-cis-Z-3-[4-dimethylaminomethyl-3-(3-hydroxy-phenyl)-cyclohexylidenemethyl]-benzoic acid, rac-cis-Z-3-[4-dimethylaminomethyl-3-hydroxy-3-(3-methoxy-phenyl)-cyclohexylidenemethyl]-benzoic acid methyl ester, rac-cis-E-3-[3-chloro-4-dimethylaminomethyl-3-(3-methoxy-phenyl)-cyclohexylidenemethyl]-benzoic acid methyl ester, rac-cis-E-3-[4-dimethylaminomethyl-3-hydroxy-3-(3-methoxy-phenyl)-cyclohexylidenemethyl]-benzoic acid methyl ester, rac-cis-Z-3-[4-dimethylaminomethyl-3-hydroxy-3-(3-methoxy-phenyl)cyclohexylidenemethyl]-benzoic acid methyl ester, (+)-trans-E-3-[4-dimethylaminomethyl-3-(3-methoxy-phenyl)-cyclohexylidenemethyl]-benzoic acid, (−)-trans-E-3-[4-dimethylaminomethyl-3-(3-methoxy-phenyl)-cyclohexylidenemethyl]-benzoic acid, rac-trans-E-3-(4-dimethylaminomethyl-3-phenyl-cyclohexylidenemethyl)-benzoic acid methyl ester, rac-trans-Z-3-(4-dimethylaminomethyl-3-phenyl-cyclohexylidenemethyl)-benzoic acid methyl ester, rac-cis-E-3-(4-dimethylaminomethyl-3-phenyl-cyclohexylidenemethyl)-benzoic acid, rac-cis-E-3-(4-dimethylaminomethyl-3-phenyl-cyclohexylidenemethyl)-benzoic acid, rac-trans-Z-3-(4-dimethylaminomethyl-3-phenyl-cyclohexylidenemethyl)benzoic acid, rac-trans-E-3-(4-dimethylaminomethyl-3-phenyl-cyclohexylidenemethyl)-benzoic acid, rac-trans-E-3-[4-dimethylaminomethyl-3-(3-trifluoromethyl-phenyl)-cyclohexylidenemethyl]-benzoic acid, rac-trans-Z-3-[4-dimethylaminomethyl-3-(3-trifluoromethyl-phenyl)-cyclohexylidenemethyl]-benzoic acid, rac-trans-E-3-[4-dimethylaminomethyl-3-(3-fluoro-phenyl)-cyclohexylidenemethyl]-benzoic acid methyl ester, rac-trans-Z-3-[4-dimethylaminomethyl-3-(3-fluoro-phenyl)-cyclohexylidenemethyl] benzoic acid methyl ester, rac-cis-E-3-[4-dimethylaminomethyl-3-(3-fluoro-phenyl)-cyclohexylidenemethyl]-benzoic acid methyl ester, rac-trans-E-3-[4-dimethylaminomethyl-3-(3-fluoro-phenyl)-cyclohexylidenemethyl]-benzoic acid, rac-trans-Z-3-[4-dimethylaminomethyl-3-(3-fluoro-phenyl)-cyclohexylidenemethyl]-benzoic acid, rac-cis-E-3-[4-dimethylaminomethyl-3-(3-fluoro-phenyl)-cyclohexylidenemethyl]-benzoic acid, E-[4-ethylidene-2-(3-methoxy-phenyl)-cyclohex-2-enylmethyl]-dimethylamine

[4-isopropylidene-2-(3-methoxy-phenyl)-cyclohex-2-enylmethyl]-dimethylamine,

E-[2-(3-methoxy-phenyl)-4-propylidene-cyclohex-2-enylmethyl]-dimethylamine, and

E-[4-butylidene-2-(3-methoxy-phenyl)-cyclohex-2-enylmethyl]-dimethylamine.

Example 44

Pharmacological Studies:

Writhing Test

The antinociceptive activity of the compounds according to the invention was investigated in mice in the phenylquinone-induced writhing test, modified by I.C. Hendershot, J. Forsaith, J. Pharmacol. Exp. Ther. 125, 237–240 (1959). Male NMRI mice weighing 25–30 g were used. Groups of 10 animals per substance dose received 0.3 ml/mouse of a 0.02% aqueous solution of phenylquinone (phenylbenzoquinone, Sigma, Deisenhofen; preparation of the solution with the addition of 5% ethanol and storage in a water bath at 45° C.) administered intraperitoneally 10 minutes after intravenous administration of a compound according to the invention. The animals were placed individually in observation cages. The number of pain-induced stretching movements (so-called writhing reactions, that is straightening of the body with stretching of the hind extremities) was counted by means of a push-button counter for 5–20 minutes after the administration of phenylquinone. Animals which received physiological saline solution i.v. and phenylquinone i.v. were also run as a control.

All substances were tested in the standard dose of 10 mg/kg. The percentage inhibition (% inhibition) of the writhing reactions by a substance was calculated according to the following equation:

$$\% \text{ inhibition}=100-(WR_{treated\ animals}/WR_{control} \times 100)$$

All compounds according to the invention investigated showed a moderate to potent analgesic action.

The results of selected writhing investigations are summarized in Table 1.

TABLE 1

Analgesia Effect in Mouse Writhing Test

| Compound | % inhibition of the writhing reactions (10 mg/kg i.v.) |
| --- | --- |
| 8 | 98 |
| 10 | 84 |
| 13 | 85 |
| 14 | 94 |
| 15 | 100 |
| 16 | 98 |
| 17 | 85 |
| 18 | 100 |
| 19 | 82 |
| 20 | 84 |
| 21 | 79 |
| 22 | 93 |
| 23 | 88 |
| 24 | 100 |
| 25 | 100 |
| 26 | 87 |
| 28 | 100 |
| 29 | 94 |
| 30 | 84 |
| 32 | 100 |
| 33 | 90 |
| 34 | 78 |
| 35 | 100 |
| 36 | 100 |
| 37 | 91 |
| 39 | 78 |
| 48 | 98 |

What is claimed is:

1. A substituted aminomethyl-phenyl-cyclohexane derivative of formula I or Ia,

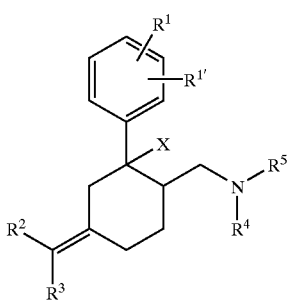

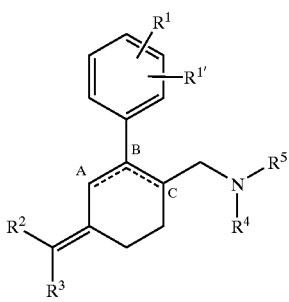

wherein
$R^1$ and $R^{1'}$ independently of one another are
H; $C_1$–$C_{10}$-alkyl, $C_2$–$C_{10}$-alkenyl or $C_2$–$C_{10}$-alkinyl, in each case branched or unbranched and mono-or polysubstituted or unsubstituted; F; Cl; Br; I; $NR^6R^{6'}$; $NO_2$; CN; $OR^6$; $SR^6$; $OC(O)R^6$; $C(O)OR^6$; $C(O)R^6$; or $C(O)NR^6R^{6'}$, wherein $R^6$ and $R^{6'}$ independently of one another are
H; $C_{1-C10}$-alkyl, $C_2$–$C_{10}$-alkenyl or $C_2$–$C_{10}$-alkinyl, in each case branched or unbranched and mono-or polysubstituted or unsubstituted; $C_3$–$C_7$-cycloalkyl, saturated or unsaturated and mono-or polysubstituted or unsubstituted, or a corresponding heterocyclic radical, in which one carbon atom in the ring is replaced by N, S or O; alkylaryl, saturated or unsaturated and mono-or polysubstituted or unsubstituted; or aryl or heteroaryl, in each case mono-or polysubstituted or unsubstituted; or $R^1$ and $R^{1'}$ together form —CH=CH—CH=CH— to form a naphthyl system which is mono-or polysubstituted, X is
H; F; Cl; Br; I; $CF_3$; $OS(O_2)C_6H_4$-$pCH_3$; or $OR^7$ or $OC(O)R^7$, wherein $R^7$ is
H; $C_{1-C10}$-alkyl, $C_2$–$C_{10}$-alkenyl or $C_2$–$C_{10}$-alkinyl, in each case branched or unbranched and mono-or polysubstituted or unsubstituted; $C_3$–$C_7$-cycloalkyl, saturated or unsaturated and mono-or polysubstituted or unsubstituted, or a corresponding heterocyclic radical, in which one carbon atom in the ring is replaced by an N, S or O; alkylaryl, saturated or unsaturated and mono-or polysubstituted or unsubstituted; or aryl or heteroaryl, in each case mono-or polysubstituted or unsubstituted; or in formula Ia where there is no X, a double bond is formed between carbon atoms "A" and "B", or carbon atoms "B" and "C", $R^4$ and $R^5$ independently of one another are
H; $C_1$–$C_{10}$-alkyl, $C_2$–$C_{10}$-alkenyl or $C_2$–$C_{10}$-alkinyl, in each case branched or unbranched and mono-or polysubstituted or unsubstituted; $C_3$–$C_7$-cycloalkyl, saturated or unsaturated and mono-or polysubstituted or unsubstituted, or a corresponding heterocyclic radical, in which one carbon atom in the ring is replaced by an N, S or O; alkylaryl, saturated or unsaturated and mono-or polysubstituted or unsubstituted; or aryl or heteroaryl, in each case mono-or polysubstituted or unsubstituted; or $R^4$ and $R^5$ together form a $C_4$–$C_7$-cycloalkyl, saturated or unsaturated and mono-or polysubstituted or unsubstituted, or a corresponding heterocyclic radical, in which one carbon atom in the ring is replaced by an S, O or $NR^8$, where $R^8$ is H; or $C_{1-C10}$-alkyl, $C_2$–$C_{10}$-alkenyl or $C_2$–$C_{10}$-alkinyl, in each case branched or unbranched and mono-or polysubstituted or unsubstituted; and $R^2$ and $R^3$ independently of one another are
$R^9$ or $YR^9$, wherein Y is $C_{1-C10}$-alkyl, $C_2$–$C_{10}$-alkenyl or $C_2$–$C_{10}$-alkinyl, branched or unbranched and mono-or polysubstituted or unsubstituted, and wherein $R^9$ is
H; F; Cl; Br; I; CN; $NO_2$; $C_1$–$C_{18}$-alkyl, $C_2$–$C_{18}$-alkenyl or alkinyl, in each case branched or unbranched and mono-or polysubstituted or unsubstituted; $C_3$–$C_7$-cycloalkyl, saturated or unsaturated and mono-or polysubstituted or unsubstituted, or a corresponding heterocyclic radical, in which one carbon atom in the ring is replaced by an S, O or $NR^{10}$, wherein $R^{10}$ is
H; or $C_{1-C10}$-alkyl, $C_2$–$C_{10}$-alkenyl or $C_2$–$C_{10}$-alkinyl, in each case branched or unbranched and mono-or polysubstituted or unsubstituted;
$OR^{11}$, $OC(O)R^{11}$, $OC(O)OR^{11}$, $OC(S)R^{11}$, $C(O)R^{11}$, $C(O)OR^{11}$, $C(S)R^{11}$, $C(S)OR^{11}$, $SR^{11}$, $S(O)R^{11}$ or $S(O_2)R^{11}$, wherein $R^{11}$ is
H; $C_1$–$C_{18}$-alkyl, $C_2$–$C_{18}$-alkenyl or $C_2$–$C_{18}$-alkinyl, in each case branched or unbranched and mono-or polysubstituted or unsubstituted; or $C_3$–$C_7$-cycloalkyl, saturated or unsaturated and mono-or polysubstituted or unsubstituted, or a corresponding heterocyclic radical, in which one carbon atom in the ring is replaced by an S, O or $NR^2$, wherein $R^2$ is
H; or $C_1$–$C_{10}$-alkyl, $C_2$–$C_{10}$-alkenyl or $C_2$–$C_{10}$-alkinyl, in each case branched or unbranched and mono-or polysubstituted or unsubstituted; alkylaryl, saturated or unsaturated and mono-or polysubstituted or unsubstituted; or aryl or heteroaryl, in each case mono-or polysubstituted or unsubstituted;
$NR^{13}R^{14}$, $NR^{13}C(O)R^{14}$, $C(O)NR^{13}R^{14}$ or $S(O_2)NR^{13}R^{14}$, wherein $R^{13}$ and $R^{14}$ independently of one another are
H; O; $C_1$–$C_{18}$-alkyl, $C_2$–$C_{18}$-alkenyl or $C_2$–$C_{18}$-alkinyl, in each case branched or unbranched and mono-or polysubstituted or unsubstituted; $C_3$–$C_7$-cycloalkyl, saturated or unsaturated and mono-or polysubstituted or unsubstituted, or a corresponding heterocyclic radical, in which one carbon atom in the ring is replaced by S, O or $NR^{15}$, wherein $R^{15}$ is
H; or $C_{1-C10}$-alkyl, $C_2$–$C_{10}$-alkenyl or alkinyl, in each case branched or unbranched and mono-or polysubstituted or unsubstituted;
alkylaryl, saturated or unsaturated and mono-or polysubstituted or unsubstituted; or aryl or heteroaryl, in each case mono-or polysubstituted or unsubstituted; or $R^{13}$ and $R^{14}$ together form a $C_3$–$C_7$-cycloalkyl, saturated or unsaturated and mono-or polysubstituted or unsubstituted, or a corresponding heterocyclic radical, in which one carbon atom in the ring is replaced by an S, O or $NR^{16}$, where $R^{16}$ is H; or $C_1$–$C_{10}$-alkyl, $C_2$–$C_{10}$-alkenyl or $C_2$–$C_{10}$-alkinyl, in each case branched or unbranched and mono-or polysubstituted or unsubstituted; or alkylaryl, aryl or heteroaryl, in each case mono-or polysubstituted or unsubstituted;

or a diastereomer or an enantiomer thereof, or a salt thereof formed with a physiologically tolerated acid, wherein in connection with alkyl, alkenyl, alkinyl, and cycloalkyl and the "corresponding heterocyclic radical," the term substituted means the replacement of a hydrogen radical by F, Cl, Br, I, $NH_2$, SH, or OH; and polysubstituted radicals means radicals which are substituted more than once either on different or on the same atom, and wherein in respect of aryl, alkylaryl or heteroaryl, mono-or polysubstituted means substitution of the ring system on one or more atoms by F; Cl; Br; I; $NH_2$: SH; OH; $CF_3$; or mono-or polysubstituted or unsubstituted $C_1$–$C_5$ alkyl, $C_1$–$C_6$ alkoxy, $C_2$–$C_8$ alkenyl, $C_2$–$C_8$ alkinyl; or aryl.

2. A hydrochloride salt of a substituted aminomethyl phenyl-cyclohexane derivative of claim 1.

3. A substituted aminomethyl-phenyl-cyclohexane derivative according to claim 1, wherein $R^9$ is

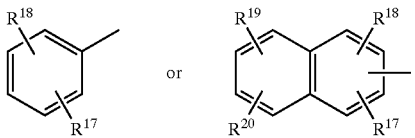

wherein $R^{17}$, $R^{18}$, $R^{19}$ and $R^{20}$ independently of one another $R^{21}$ are or $ZR^{21}$, wherein Z is $C_{1-C10}$-alkyl, $C_2$–$C_{10}$-alkenyl or $C_2$–$C_{10}$-alkinyl, in each case branched or unbranched and mono-or polysubstituted or unsubstituted, and $R^{21}$ is H; F; Cl; Br; I; CN; $NO_2$; $C_1$–$C_{18}$-alkyl, $C_2$–Cis-alkenyl or $C_2$–Cis-alkinyl, in each case branched or unbranched and mono-or polysubstituted or unsubstituted; $C_3$–$C_7$-cycloalkyl, saturated or unsaturated and mono-or polysubstituted or unsubstituted, or a corresponding heterocyclic radical, in which one carbon atom in the ring is replaced by an S, 0 or $NR^{22}$, wherein $R^{22}$ is H; or $C_{1-C10}$-alkyl, $C_2$–$C_{10}$-alkenyl or $C_2$–$C_{10}$-alkinyl, in each case branched or unbranched and mono-or polysubstituted or unsubstituted;

alkylaryl, aryl or heteroaryl, in each case mono-or polysubstituted or unsubstituted;

$OR^{23}$, $OC(O)R^{23}$, $OC(O)OR^{23}$, $OC(S)R^{23}$, $C(O)R^{23}$, $C(O)OR^{23}$, $C(S)R^{23}$, $C(S)OR^{23}$, $SR^{23}$, $S(O)R^{23}$ or $S(02)R^{23}$, wherein $R^{23}$ is H; $C_1$–$C_{18}$-alkyl, $C_2$–$C_{18}$-alkenyl or $C_2$–$C_{18}$-alkinyl, in each case branched or unbranched and mono-or polysubstituted or unsubstituted; $C_3$–$C_7$-cycloalkyl, saturated or unsaturated and mono-or polysubstituted or unsubstituted, or a corresponding heterocyclic radical, in which one carbon atom in the ring is replaced by an S, O or $NR^{24}$, $R^{24}$, wherein $R^{24}$ is H; or $C_{1-C10}$-alkyl, $C_2$–$C_{10}$-alkenyl or $C_2$–$C_{10}$-alkinyl, in each case branched or unbranched and mono-or polysubstituted or unsubstituted;

or alkylaryl, saturated or unsaturated and mono-or polysubstituted or unsubstituted; aryl or heteroaryl, in each case mono-or polysubstituted or unsubstituted; or $NR^{25}R^{26}$, $NR^{25}C(O)R^{26}$, $C(O)NR^{25}R^{26}$ or $S(02)NR^{25}R^{26}$, wherein $R^{25}$ and $R^{26}$ independently of one another are H; $C_1$-$C_{18}$-alkyl, $C_2$–$C_{18}$-alkenyl or $C_2$–$C_{18}$-alkinyl, in each case branched or unbranched and mono-or polysubstituted or unsubstituted; $C_3$–$C_7$-cycloalkyl, saturated or unsaturated and mono-or polysubstituted or unsubstituted, or a corresponding heterocyclic radical, in which one C atom in the ring is replaced by S, O or $NR^{27}$ where $R^{27}$ is H; or $C_{1-C10}$-alkyl, $C_2$–$C_{10}$-alkenyl or $C_2$–$C_{10}$-alkinyl, in each case branched or unbranched and mono-or polysubstituted or unsubstituted; alkylaryl, saturated or unsaturated and mono-or polysubstituted or unsubstituted; or aryl or heteroaryl, in each case mono-or polysubstituted or unsubstituted; or $R^{25}$ and $R^{26}$ together form a $C_3$–$C_7$-cycloalkyl, saturated or unsaturated and mono-or polysubstituted or unsubstituted, or a corresponding heterocyclic radical in which one carbon atom in the ring is replaced by an S, O or $NR^{28}$, wherein $R^{28}$ is H, $C_{1-C10}$-alkyl, $C_2$–$C_{10}$-alkenyl or $C_2$–$C_{10}$-alkinyl, in each case branched or unbranched and mono-or polysubstituted or unsubstituted.

4. A substituted aminomethyl-phenyl-cyclohexane derivative according to claim 1, wherein $R^2$ is different from $R^3$.

5. A substituted aminomethyl-phenyl-cyclohexane derivative according to claim 4, wherein $R^3$ is H or $CH_3$.

6. A substituted aminomethyl-phenyl-cyclohexane derivative according to claim 5, wherein $R^3$ is H.

7. A substituted aminomethyl-phenyl-cyclohexane derivative according to claim 1, wherein $R^2$ is

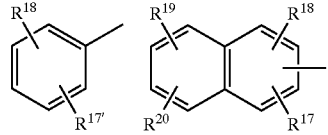

or $C_{1-3}$-alkyl, wherein $R^{17}$, $R^{18,\ R19}$ and $R^{20}$ independently of one another are $R^{21}$ or $ZR^{21}$, wherein Z is $C_{1-C10}$-alkyl, $C_2$–$C_{10}$-alkenyl or $C_2$–$C_{10}$-alkinyl, in each case branched or unbranched and mono-or polysubstituted or unsubstituted, and $R^{21}$ is H; F; Cl; Br; I; CN; $NO_2$; $C_1$–$C_{18}$-alkyl, $C_2$–$C_{18}$-alkenyl or $C_2$–$C_{18}$-alkinyl, in each case branched or unbranched and mono-or polysubstituted or unsubstituted; $C_3$–$C_7$-cycloalkyl, saturated or unsaturated and mono-or polysubstituted or unsubstituted, or a corresponding heterocyclic radical, in which one carbon atom in the ring is replaced by an S, O or $NR^{22}$, wherein $R^{22}$ is H; or $C_{1-C10}$-alkyl, $C_2$–$C_{10}$-alkenyl or $C_2$–$C_{10}$-alkinyl, in each case branched or unbranched and mono-or polysubstituted or unsubstituted;

alkylaryl, aryl or heteroaryl, in each case mono-or polysubstituted or unsubstituted;

$OR^{23}$, $OC(O)R^{23}$, $OC(O)OR^{23}$, $OC(S)R^{23}$, $C(O)R^{23}$, $C(O)OR^{23}$, $C(S)R^{23}$, $C(S)OR^{23}$, $SR^{23}$, $S(O)R^{23}$ or $S(O_2)R^{23}$, wherein $R^{23}$ is H; $C_1$–$C_{18}$-alkyl, $C_2$–Cis-alkenyl or $C_2$–Cis-alkinyl, in each case branched or unbranched and mono-or polysubstituted or unsubstituted; $C_3$–$C_7$-cycloalkyl, saturated or unsaturated and mono-or polysubstituted or unsubstituted, or a corresponding heterocyclic radical, in which one carbon atom in the ring is replaced by an S, O or $NR^{24}$, wherein $R^{24}$ is H; or $C_{1-C10}$-alkyl, $C_2$–$C_{10}$-alkenyl or $C_2$–$C_{10}$-alkinyl, in each case branched or unbranched and mono-or polysubstituted or unsubstituted;

or alkylaryl, saturated or unsaturated and mono-or polysubstituted or unsubstituted; aryl or heteroaryl, in each case mono-or polysubstituted or unsubstituted; or $NR^{25}R^{26}$, $NR^{25}C(O)R^{26}$, $C(O)NR^{25}R^{26}$ or $S(O_2)NR^{25}R^{26}$, wherein $R^{25}$ and $R^{26}$ independently of one another are H; $C_1$–$C_{18}$-alkyl, $C_2$–$C_{18}$-alkenyl or $C_2$–$C_{18}$-alkinyl, in each case branched or unbranched and mono-or polysubstituted or unsubstituted; $C_3$–$C_7$-cycloalkyl, saturated or unsaturated and mono-or polysubstituted or unsubstituted, or a corresponding heterocyclic radical, in which one C atom in the ring is replaced by S, O or $NR^{27}$, where $R^{27}$ is H; or $C_{1-C10}$-alkyl, $C_2$–$C_{10}$-alkenyl or $C_2$–$C_{10}$--alkinyl, in each case branched or unbranched and mono-or polysubstituted or unsubstituted;

alkylaryl, saturated or unsaturated and mono-or polysubstituted or unsubstituted; or aryl or heteroaryl, in each case mono-or polysubstituted or unsubstituted; or $R^{25}$ and $R^{26}$ together form a $C_4$–$C_7$-cycloalkyl, saturated or unsaturated and mono-or polysubstituted or unsubstituted, or a corresponding heterocyclic radical in which one carbon atom in the ring is replaced by an S, O or $NR^{28}$, wherein $R^{28}$ is H, $C_{1-C10}$-alkyl, $C_2$–$C_{10}$-alkenyl or $C_2$–$C_{10}$-alkinyl, in each case branched or unbranched and mono-or polysubstituted or unsubstituted.

8. A substituted aminomethyl-phenyl-cyclohexane derivative according to claim 7, wherein $R^{19}$ and $R^{20}$ are H.

9. A substituted aminomethyl-phenyl-cyclohexane derivative according to claim 7, wherein $R^{12}$ is

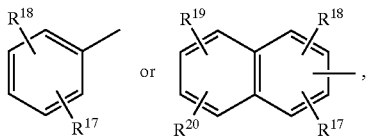

wherein $R^{17}$ is different from $R^{18}$.

10. A substituted aminomethyl-phenyl-cyclohexane derivative according to claim 7, wherein $R^{12}$ is

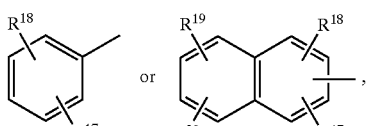

wherein $R^{18}$ and $R^{21}$ are the same and are selected from the group consisting of H, F, Cl, Br, I, $CF_3$ and $OR^{23}$, wherein $R^{23}$ is H, methyl ethyl, propyl, isopropyl, butyl or isobutyl.

11. A substituted aminomethyl-phenyl-cyclohexane derivative according to claim 1, wherein $R^2$ is

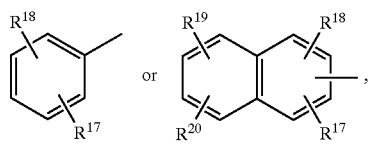

wherein $R^{17}$ is
$R^{21}$, wherein $R^{21}$ is
H; F; Cl; Br; I; $CF_3$; $OR^{23}$; $OC(O)R^{23}$; $C(O)R^{23}$; or $C(O)OR^{23}$, wherein $R^{23}$ is
H; $C_1$–$C_6$-alkyl, $C_2$–$C_8$-alkenyl or $C_2$–$C_8$-alkinyl, branched or unbranched and mono-or polysubstituted or unsubstituted; or $C(O)NR^{25}R^{26}$, wherein $R^{25}$ and $R^{26}$ independently of one another are
H; O; or $C_1$–$C_{18}$-alkyl, branched or unbranched, saturated or unsaturated and mono-or polysubstituted or unsubstituted;

or wherein $R^{17}$ is $ZR^{21}$, wherein
Z is $CH_2$ or $C_2H_4$, and
$R^{21}$ is
$OR^{23}$, $OC(O)R^{23}$, $C(O)R^{23}$ or $C(O)OR^{23}$, wherein $R^{23}$ is chosen from
H; $C_1$–$C_6$-alkyl, $C_2$–$C_8$-alkenyl or $C_2$–$C_8$-alkinyl, in particular $C_1$–$C_4$-alkyl, branched or unbranched and mono-or polysubstituted or unsubstituted; or $C(O)NR^{25}R^{26}$, wherein $R^{25}$ and $R^{26}$ independently of one another are
H; O; or $C_1$–$C_{18}$-alkyl, branched or unbranched, saturated or unsaturated and mono-or polysubstituted or unsubstituted;

and wherein $R^{18}$, $R^{19}$ and $R^{20}$ independently of one another are or $ZR^{21}$, wherein
$R^{21}$ or $ZR^{21}$, wherein
Z is $C_{1-C10}$-alkyl, $C_2$–$C_{10}$-alkenyl or $C_2$–$C_{10}$-alkinyl, in each case branched or unbranched and mono-or polysubstituted or unsubstituted, and
$R^{21}$ is H; F; Cl; Br; I; CN; $NO_2$; $C_1$–$C_{18}$-alkyl, $C_2$–$C_{18}$-alkenyl or $C_2$–$C_{18}$-alkinyl, in each case branched or unbranched and mono-or polysubstituted or unsubstituted; $C_3$–$C_7$-cycloalkyl, saturated or unsaturated and mono-or polysubstituted or unsubstituted, or a corresponding heterocyclic radical, in which one carbon atom in the ring is replaced by an S, O or $NR^{22}$, wherein $R^{22}$ is
H; or $C_{1-C10}$-alkyl, $C_2$–$C_{10}$-alkenyl or $C_2$–$C_{10}$-alkinyl, in each case branched or unbranched and mono-or polysubstituted or unsubstituted;
alkylaryl, aryl or heteroaryl, in each case mono-or polysubstituted or unsubstituted;
$OR^{23}$, $OC(O)R^{23}$, $OC(O)OR^{23}$, $OC(S)R^{23}$, $C(O)R^{23}$, $C(O)OR^{23}$, $C(S)R^{23}$, $C(S)OR^{23}$, $SR^{23}$, $S(O)R^{23}$ or $S(02)R^{23}$, wherein $R^{23}$ is
H; $C_1$–$C_{10}$-alkyl, $C_2$–$C_{18}$-alkenyl or $C_2$–Cis-alkinyl, in each case branched or unbranched and mono-or polysubstituted or unsubstituted; $C_2$–$C_7$-cycloalkyl, saturated or unsaturated and mono-or polysubstituted or unsubstituted, or a corresponding heterocyclic radical, in which one carbon atom in the ring is replaced by an S, O or $NR^{24}$, wherein $R^{24}$ is
H; or $C_{1-C10}$-alkyl, $C_2$–$C_{10}$-alkenyl or $C_2$–$C_{10}$-alkinyl, in each case branched or unbranched and mono-or polysubstituted or unsubstituted;
alkylaryl, saturated or unsaturated and mono-or polysubstituted or unsubstituted; or aryl or heteroaryl, in each case mono-or polysubstituted or unsubstituted; or NR$^{25}$R$^{26}$, NR$^{25}$C(O)R$^{26}$, C(O)NR$^{25}$R$^{26}$ or S(O$_2$)NR$^{25}$R$^{26}$, wherein R$^{25}$ and R$^{26}$ independently of one another are H; C$_1$–C$_{18}$-alkyl, C$_2$–C$_{18}$-alkenyl or C$_2$–Cis-alkinyl, in each case branched or unbranched and mono-or polysubstituted or unsubstituted; C$_3$–C$_7$-cycloalkyl, saturated or unsaturated and mono-or polysubstituted or unsubstituted, or a corresponding heterocyclic radical, in which one C atom in the ring is replaced by S, O or NR$^{27}$, where R$^{27}$ is H; or C$_{1-C10}$-alkyl, C$_2$–C$_{10}$-alkenyl or C$_2$–C$_{10}$--alkinyl, in each case branched or unbranched and mono-or polysubstituted or unsubstituted; alkylaryl, saturated or unsaturated and mono- or polysubstituted or unsubstituted; or aryl or heteroaryl, in each case mono-or polysubstituted or unsubstituted; or R$^{25}$ and R$^{26}$ together form a C$_3$–C$_7$-cycloalkyl, saturated or unsaturated and mono-or polysubstituted or unsubstituted, or a corresponding heterocyclic radical in which one carbon atom in the ring is replaced by an S, O or NR$^{28}$, wherein R$^{28}$ is H; or C$_{1-C10}$-alkyl, C$_2$–C$_{10}$-alkenyl or C$_2$–C$_{10}$-alkinyl, in each case branched or unbranched and mono-or polysubstituted or unsubstituted.

12. A substituted aminomethyl-phenyl-cyclohexane derivative according to claim 11, wherein R$^{23}$ is branched or unbranched and mono-or polysubstituted or unsubstituted C$_1$–C$_4$-alkyl.

13. A substituted aminomethyl-phenyl-cyclohexane derivative according to claim 12, wherein R$^{23}$ is H, methyl ethyl, propyl, isopropyl, butyl or isobutyl.

14. A substituted aminomethyl-phenyl-cyclohexane derivative according to claim 13, wherein R$^{23}$ is H, CH$_3$, C$_2$H$_5$ or isobutyl.

15. A substituted aminomethyl-phenyl-cyclohexane derivative according to claim 11, wherein R$^{25}$ and R$^{26}$ independently of one another are branched or unbranched, saturated or unsaturated and mono-or polysubstituted or unsubstituted C$_1$–C$_4$-alkyl.

16. A substituted aminomethyl-phenyl-cyclohexane derivative according to claim 11, wherein wherein R$^{25}$ and R$^{26}$ independently of one another are H, methyl ethyl, propyl, isopropyl, butyl or isobutyl.

17. A substituted aminomethyl-phenyl-cyclohexane derivative according to claim 11, wherein wherein R$^{25}$ and R$^{26}$ independently of one another are C$_2$H$_5$.

18. A substituted aminomethyl-phenyl-cyclohexane derivative according to claim 11, wherein the R$^{21}$ in the ZR$^{21}$ of R$^{17}$ is OR$^{23}$.

19. A substituted aminomethyl-phenyl-cyclohexane derivative according to claim 18, wherein the R$^{21}$ in the ZR$^{21}$ of R$^{17}$ is OR$^{23}$, which R$^{23}$ is H, methyl ethyl, propyl, isopropyl, butyl or isobutyl.

20. A substituted aminomethyl-phenyl-cyclohexane derivative according to claim 19, wherein the R$^{21}$ in the ZR$^{21}$ of R$^{17}$ is OR$^{28}$, which R$^{23}$ is H.

21. A substituted aminomethyl-phenyl-cyclohexane derivative according to claim 11, wherein in the C(O)NR$^{25}$R$^{26}$ of R$^{17}$, R$^{25}$ and R$^{26}$ independently of one another are branched or unbranched, saturated or unsaturated and mono-or polysubstituted or unsubstituted C$_{1-C4}$-alkyl.

22. A substituted aminomethyl-phenyl-cyclohexane derivative according to claim 11, wherein in the C(O)NR$^{25}$R$^{26}$ of R$^{17}$, R$^{25}$ and R$^{26}$ independently of one another are H, methyl ethyl, propyl, isopropyl, butyl or isobutyl.

23. An aminomethyl-phenyl-cyclohexane derivative according to claim 11, wherein the R$^{21}$ of R$^{17}$ is H, F, Cl, C(O)OR$^{23}$.

24. A substituted aminomethyl-phenyl-cyclohexane derivative according to claim 1, wherein R$^1$ is selected from the group consiting of from H, F, Cl, Br, I, CF$_3$, SCH$_3$ and OR$^6$, wherein R$^6$ is H, or branched or unbranched and mono-or polysubstituted or unsubstituted C$_1$–C$_4$-alkyl.

25. A substituted aminomethyl-phenyl-cyclohexane derivative according to claim 24, wherein R$^1$ is OR$^6$.

26. A substituted aminomethyl-phenyl-cyclohexane derivative according to claim 25, wherein R$^1$ is OH or OCH$_3$.

27. A substituted aminomethyl-phenyl-cyclohexane derivative according to claim 1, wherein R$^{1'}$ is H, F, Cl, SCH$_3$ or OCH$_3$.

28. A substituted aminomethyl-phenyl-cyclohexane derivative according to claim 1, wherein R$^{1'}$ is H.

29. A substituted aminomethyl-phenyl-cyclohexane derivative according to claim 24, wherein R$^{1'}$ is H, F, Cl, SCH$_3$ or OCH$_3$.

30. A substituted aminomethyl-phenyl-cyclohexane derivative according to claim 1, wherein X is H, F, Br, I, Cl or OR$^7$; or if according to formula Ia the compound contains no X, a double bond is formed between carbon atoms "A" and "B", or between carbon atoms "B" and "C".

31. A substituted aminomethyl-phenyl-cyclohexane derivative according to claim 30, wherein X is H, F, Cl, OH, or OCH$_3$.

32. A substituted aminomethyl-phenyl-cyclohexane derivative according to claim 31, wherein X is H.

33. A substituted aminomethyl-phenyl-cyclohexane derivative according to claim 24, wherein X is H, F, Br, I, Cl or OR$^7$; or if the compound contains no X, according to formula Ia a double bond is formed between carbon atom A and carbon atom B, or between carbon atom B and carbon atom C.

34. A substituted aminomethyl-phenyl-cyclohexane derivative according to claim 27, wherein X is H, F, Br, I, Cl or OR$^7$; or if according to formula Ia the compound contains no X, a double bond is formed between carbon atoms "A" and "B", or between carbon atoms "B" and "C".

35. A substituted aminomethyl-phenyl-cyclohexane derivative according to claim 29, wherein X is H, F, Br, I, Cl or OR$^7$; or if according to formula Ia the compound contains no X, a double bond is formed between carbon atoms "A" and "B", or between carbon atoms "B" and "C".

36. A substituted aminomethyl-phenyl-cyclohexane derivative according to claim 1, wherein R$^4$ and R$^5$ independently of one another are branched or unbranched and mono-or polysubstituted or unsubstituted C$_1$–C$_4$-alkyl.

37. A substituted aminomethyl-phenyl-cyclohexane derivative according to claim 36, wherein R$^4$ and R$^5$ independently of one another are CH$_3$.

38. A substituted aminomethyl-phenyl-cyclohexane derivative according to claim 24, wherein R$^4$ and R$^5$ independently of one another are branched or unbranched and mono-or polysubstituted or unsubstituted C$_1$–C$_4$-alkyl.

39. A substituted aminomethyl-phenyl-cyclohexane derivative according to claim 27, wherein R$^4$ and R$^5$ independently of one another are branched or unbranched and mono-or polysubstituted or unsubstituted C$_1$–C$_4$-alkyl.

40. A substituted aminomethyl-phenyl-cyclohexane derivative according to claim 29, wherein R$^4$ and R$^5$ independently of one another are branched or unbranched and mono-or polysubstituted or unsubstituted $C_1$–$C_4$-alkyl.

41. A substituted aminomethyl-phenyl-cyclohexane derivative according to claim 33, wherein $R^4$ and $R^5$ independently of one another are branched or unbranched and mono-or polysubstituted or unsubstituted $C_1$–$C_4$-alkyl.

42. A substituted aminomethyl-phenyl-cyclohexane derivative according to claim 35, wherein $R^4$ and $R^5$ independently of one another are branched or unbranched and mono-or polysubstituted or unsubstituted $C_1$–$C_4$-alkyl.

43. A substituted aminomethyl-phenyl-cyclohexane derivative according to claim 1, wherein $R^1$ is OH or $OCH_3$, $R^{1'}$ is H, X is H, $R^4$ is $CH_3$ and $R^5$ is $CH_3$.

44. A substituted aminomethyl-phenyl-cyclohexane derivative according claim 1, selected from the group consisting of:

rac-cis-E-[4-benzylidene-2-(3-methoxy-phenyl)-cyclohexylmethyl]-dimethylamine, rac-trans-E-[4-benzylidene-2-(3-methoxy-phenyl)-cyclohexylmethyl]-dimethylamine, rac-trans-Z-[4-benzylidene-2-(3-methoxy-phenyl)-cyclohexylmethyl]-dimethylamine, rac-cis-Z-[4-benzylidene-2-(3-methoxy-phenyl)-cycllheylmethyl]-dimethylamine, rac-cis-E-3-[4-dimethylaminomethyl-3-(3-methoxy-phenyl)-cyclohexylidenemethyl]-benzoic acid methyl ester, rac-cis-Z-3-[4-dimethylaminomethyl-3-(3-methoxy-phenyl)-cyclohexylidenemethyl]-benzoic acid methyl ester, rac-trans-Z-3-[4-dimethylaminomethyl-3-(3-methoxy-phenyl)-cyclohexylidenemethyl]-benzoic acid methyl ester, rac-trans-E-3-[4-dimethylaminomethyl-3-(3-methoxy-phenyl)-cyclohexylidenemethyl]-benzoic acid methyl ester, Z-3-[4-dimethylaminomethy-3-(3-methoxy-phenyl)-2-methyl-cyclohex-2-enylidenemethyl]-benzoic acid methyl ester, E-3-[4-dimethylaminomethyl-3-(3-methoxy-phenyl)-2-methyl-cyclohex-2-enylidenemethyl]-benzoic acid methyl ester, Z-3-[4-dimethylaminomethyl-3-(3-methoxy-phenyl)-2-methyl-cyclohex-2-enylidenemethyl]-naphthalene-1-carboxylic acid ethyl ester, E-3-[4-dimethylaminomethyl-3-(3-methoxy-phenyl)-2-methyl-cyclohex-2-enylidenemethyl]-naphthalene-1-carboxylic acid ethyl ester, Z-3-[4-dimethylaminomethyl-3-(3-methoxy-phenyl)-cyclohexylidenemethyl]-2-fluoro-benzoic acid ethyl ester, Z-3-[4-dimethylaminomethyl-3-(3-methoxy-phenyl)-cyclohex-2-enylidenemethyl]-benzoic acid, E-3-[4-dimethylaminomethyl 3-(3-methoxy-phenyl)-cyclohex-2-enylidenemethyl]-benzoic acid, E-{3-[4-dimethylaminomethyl-3-(3-methoxy-phenyl)-cyclohex-2-enylidenemethyl]-phenyl}-methanol, rac-trans-Z-3-[4-dimethylaminomethyl-3-(3-methoxy-phenyl)-cyclohexylidenemethyl]-benzoic acid, rac-trans-E-3-[4-dimethylaminomethyl-3-(3-methoxy-phenyl)-cyclohexylidenemethyl]-benzoic acid, rac-trans-E-[3-(2-dimethylaminomethyl-5-(3-hydroxymethyl-benzylidene)-cyclohexyl)-phenol, rac-trans-E-3-(5-benzylidene-2-dimethylaminomethyl-cyclohexyl)-phenol, E-3-[4-dimethylaminomethyl 3-(3-methoxy-phenyl)-cyclohex-2-enylidenemethyl]-benzoic acid tert-butyl ester, E-3-[6-dimethylaminomethyl-3-(3-hydroxymethyl-benzylidene)-cyclohex-1-enyl]-phenol, rac-trans-Z-3-(5-benzylidene-2-dimethylaminomethyl-cyclohexyl)-phenol, Z-3-[2-dimethylaminomethyl-5-(3-hydroxymethyl-benzylidene)-cyclohex-1-enyl]-phenol, Z-{3-[4-dimethylaminomethyl-3-(3-methoxy-phenyl)-cyclohex-2-enylidenemethyl]-phenyl}-methanol, rac-cis-E-3-[4-dimethylaminomethyl-3-(3-methoxy-phenyl)-cyclohexylidenemethyl]-benzoic acid, rac-cis-Z-3-[4-dimethylaminomethyl-3-(3-methoxy-phenyl)-cyclohexylidenemethyl]-benzoic acid, rac-trans-E-3-[4-dimethylaminomethyl-3-(3-methoxy-phenyl)-cyclohexylidenemethyl]-benzoic acid tert-butyl ester, rac-trans-E-[3-4-dimethylaminomethyl-3-(3-methoxy-phenyl)-cyclohexylidenemethyl]-phenyl)-methanol, rac-cis-Z-3-[4-dimethylaminomethyl-3-(3-methoxy-phenyl)-cyclohexylidenemethyl]-benzoic acid ethyl ester, E-3-[4-dimethylaminomethyl-3-(3-methoxy-phenyl)-cyclohex-2-enylidenemethyl]-N,N-diethyl-benzamide, rac-trans-E-3-[4-dimethylaminomethyl-3-(3-methoxy-phenyl)-cyclohex-2-enylidenemethyl]-N,N-diethyl-benzamide, E-3-[4-dimethylaminomethyl-3-(3-methoxy-phenyl)-cyclohex-2-enylidenemethyl]-benzoic acid ethyl ester, Z-3-[4-dimethylaminomethyl-3-(3-methoxy-phenyl)-cyclohex-2-enylidenemethyl]-N,N-diethyl-benzamide, rac-cis-E-3-[4-dimethylaminomethyl-3-(3-methoxy-phenyl)-cyclohexylidenemethyl]-N,N-diethyl-benzamide, rac-trans-Z-3-[4-dimethylaminomethyl-3-(3-methoxy-phenyl)-cyclohexylidenemethyl]-N,N-diethyl-benzamide, E-3-[4-dimethylaminomethyl-3-(3-hydroxy-phenyl)-cyclohex-2-enylidenemethyl]-benzoic acid methyl ester, Z-3-[4-dimethylaminomethyl-3-(3-hydroxy-phenyl)-cyclohex-2-enylidenemethyl]-benzoic acid methyl ester, Z-3-[4-dimethylaminomethyl-3-(3-methoxy-phenyl)-cyclohex-2-enylidenemethyl]-benzoic acid isobutyl ester, Z-3-[6-dimethylaminomethyl-3-(3-hydroxymethyl-benzylidene)-cyclohex-1-enyl]-phenol, Z-[4-(4-chloro-benzylidene)-2-(3-methoxy-phenyl)-cyclohex-2-enylmethyl]-dimethyl-amine, E-[4-(4-fluoro-benzylidene)-2-(3-methoxy-phenyl)-cyclohex-2-enylmethyl]-dimethyl-amine, Z-[4-(4-fluoro-benzylidene)-2-(3-methoxy-phenyl)-cyclohex-2-enylmethyl]-dimethyl-amine, E-3-[6-dimethylaminomethyl-3-(4-fluoro-benzylidene)-cyclohex-1-enyl]-phenol, Z-3-[6-dimethylaminomethyl-3-(4-fluoro-benzylidene)-cyclohex-1-enyl]-phenol, E-[4-(4-chloro-benzylidene)-2-(3-methoxy-phenyl)-cyclohex-2-enylmethyl]-dimethyl-amine, E-3-[3-(4-chloro-benzylidene)-6-dimethylaminomethyl-cyclohex-1-enyl]-phenol, Z-3-[4-dimethylaminomethyl-3-(3-hydroxy-phenyl)-cyclohex-2-enylidenemethyl]-benzoic acid methyl ester,
E-3-[4-dimethylaminomethyl-3-(3-hydroxy-phenyl)-cyclohex-2-enylidenemethyl]-benzoic acid,
rac-cis-E-3-[4-dimethylaminomethyl-3-(3-hydroxy-phenyl)-cyclohexylidenemethyl]-benzoic acid methyl ester,
rac-cis-Z-3-[4-dimethylaminomethyl-3-(3-hydroxy-phenyl)-cyclohexylidenemethyl]-benzoic acid methyl ester,
rac-trans-Z-3-[4-dimethylaminomethyl-3-(3-hydroxy-phenyl)-cyclohexylidenemethyl]-benzoic acid,
rac-trans-E-3-[4-dimethylaminomethyl-3-(3-hydroxy-phenyl)-cyclohexylidenemethyl]-benzoic acid,
rac-cis-Z-3-[4-dimethylaminomethyl-3-(3-hydroxy-phenyl)-cyclohexylidenemethyl]-benzoic acid,
rac-cis-Z-3-[4-dimethylaminomethyl-3-hydroxy-3-(3-methoxy-phenyl)-cyclohexylidenemethyl]-benzoic acid methyl ester,
rac-cis-E-3-[3-chloro-4-dimethylaminomethyl. 3-(3-methoxy-phenyl)-cyclohexylidenemethyl]-benzoic acid methyl ester,
rac-cis-E-3-[4-dimethylaminomethyl-3-hydroxy-3-(3-methoxy-phenyl)-cyclohexylidenemethyl]-benzoic acid methyl ester,
rac-cis-Z-3-[4-dimethylaminomethyl-3-hydroxy-3-(3-methoxy-phenyl)-cyclohexylidenemethyl]-benzoic acid methyl ester,
(+)-trans-E-3-[4-dimethylaminomethyl-3-(3-methoxy-phenyl)-cyclohexylidenemethyl]-benzoic acid,
(−)-trans-E-3-[4-dimethylaminomethyl-3-(3-methoxy-phenyl)-cyclohexylidenemethyl]-benzoic acid,
rac-trans-E-3-(4-dimethylaminomethyl-3-phenyl-cyclohexylidenemethyl)-benzoic acid methyl ester,
rac-trans-Z-3-(4-dimethylaminomethyl-3-phenyl-cyclohexylidenemethyl)-benzoic acid methyl ester,
rac-cis-E-3-(4-dimethylaminomethyl-3-phenyl-cyclohexylidenemethyl)-benzoic acid,
rac-cis-E-3-(4-dimethylaminomethyl-3-phenyl-cyclohexylidenemethyl)-benzoic acid,
rac-trans-Z-3-(4-dimethylaminomethyl-3-phenyl-cyclohexylidenemethyl)-benzoic acid,
rac-trans-E-3-(4-dimethylaminomethyl-3-phenyl-cyclohexylidenemethyl)-benzoic acid,
rac-trans-E-3-[4-dimethylaminomethyl-3-(3-triflluoromethyl-phenyl)-cyclohexylidenemethyl]-benzoic acid,
rac-trans-Z-3-[4-dimethylaminomethyl-3-(3-trifluoromethyl-phenyl)-cyclohexylidenemethyl]-benzoic acid,
rac-trans-E-3-[4-dimethylaminomethyl-3-(3-fluoro-phenyl)-cyclohexylidenemethyl]-benzoic acid methyl ester,
rac-trans-Z-3-[4-dimethylaminomethyl-3-(3-fluoro-phenyl)-cyclohexylidenemethyl] benzoic acid methyl ester,
rac-cis-E-3-[4-dimethylaminomethyl-3-(3-fluoro-phenyl)-cyclohexylidenemethyl]-benzoic acid methyl ester,
rac-trans-E-3-[4-dimethylaminomethyl-3-(3-fluoro-phenyl)-cyclohexylidenemethyl]-benzoic acid,
rac-trans-Z-3-[4-dimethylaminomethyl-3-(3-fluoro-phenyl)-cyclohexylidenemethyl]-benzoic acid,
rac-cis-E-3-[4-dimethylaminomethyl-3-(3-fluoro-phenyl)-cyclohexylidenemethyl]-benzoic acid,
E-[4-ethylidene-2-(3-methoxy-phenyl)-cyclohex-2-enylmethyl]-dimethylamine,
[4-isopropylidene-2-(3-methoxy-phenyl)-cyclohex-2-enylmethyl]-dimethylamine,
E-[2-(3-methoxy-phenyl)-4-propylidene-cyclohex-2-enylmethyl]-dimethylamine, and
E-[4-butylidene-2-(3-methoxy-phenyl)-cyclohex-2-enylmethyl]-dimethylamine,
and pharmaceutically acceptable salts thereof.

45. A compound according to claim 44, wherein the compound is a pharmaceutically acceptable hydrochloride salt.

46. A process for the preparation of a substituted aminomethyl-phenyl-cyclohexane according to claim 1, wherein a cyclohexanone of formula II or II

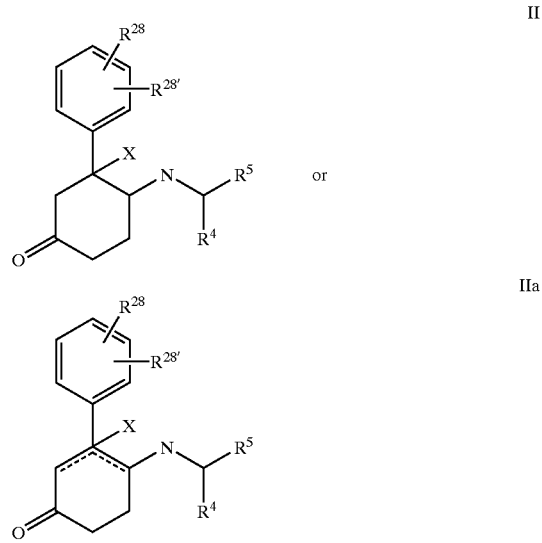

wherein $R^{28}=R^1$ and $R^{28'}=R^{1'}$, are reacted in a Wittig reaction in an organic solvent in the presence of a base with an alkyltriphenylphosphonium salt of formula III

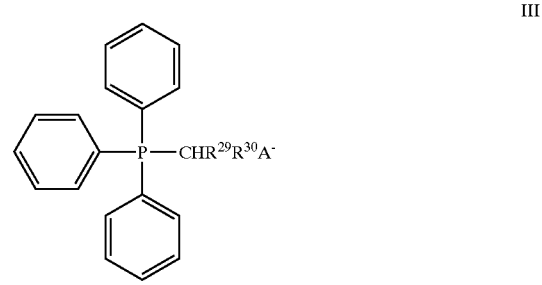

wherein A denotes chloride or bromide, $R^{29}=R^2$, and $R^{30}=R^3$.

47. A process according to claim 46, wherein the organic solvent is selected from the group consisting of benzene, toluene and a chlorinated hydrocarbon.

48. A process according to claim 46, wherein the base is potassium tert-butylate or sodium hydride.

49. A process according to claim 47, wherein the base is potassium tert-butylate or sodium hydride.

50. A process according to claim 46, wherein the Wittig reaction temperature is between 50° C. and 90° C.

51. A process according to claim 49, wherein the Wittig reaction temperature is between 50° C. and 90° C.

52. A process according to claim 46, wherein the temperature during the entire reaction is 50° C. and 90° C.

53. A process according to claim 46, wherein one or more of the following conditions are met:
(1) at least one of $R^{28}$, $R^{28'}$, $R^{29}$, and $R^{30}$ is an OH group, and the at least one OH group is replaced by an $OSi(Ph)_2$tert-but group, and after conclusion of the Wittig reaction, the OSi(Ph)2tert-but group is removed with tetrabutylammonium fluoride in tetrahydrofuran;
(2) at least one of $R^{28}$, $R^{28'}$, $R^{29}$, and $R^{30}$ is an SH group, and the at least one SH group has been replaced by an S-p-methoxybenzyl group, and after conclusion of the Wittig reaction, the p-methoxybenzyl group is removed with a metal amine; and
(3) at least one of $R^{28}$, $R^{28'}$, $R^{29}$, and $R^{30}$ is an $NH_2$ group, and the at least one $NH_2$ group is replaced by an $NO_2$ group, and after conclusion of the Wittig reaction, the $NO_2$ group is reduced to $NH_2$.

54. A process according to claim 53, wherein the metal amine for removing the S-p-methoxybenzyl group is a sodium amine.

55. A process according to claim 46, wherein a product after the Wittig reaction comprises at least one $C(O)OCH_3$ group or $C(S)OCH_3$ group, and the at least one $C(O)OCH_3$ group or $C(S)OCH_3$ group is hydrolyzed with a KOH solution or NaOH solution in methanol at a temperature of 40° C. to 60° C.

56. A pharmaceutical composition comprising a substituted aminomethyl-phenyl-cyclohexane derivative according to claim 1, in the form of a diastereomer, enantiomer, or of a salt formed with a physiologically tolerated acid.

57. A pharmaceutical composition according to claim 56, wherein the salt is a hydrochloride salt.

58. A pharmaceutical composition of claim 56, wherein the substituted aminomethyl-phenyl-cyclohexane derivative is selected from the group consisting of:
rac-cis-E-[4-benzylidene-2-(3-methoxy-phenyl)-cyclohexylmethyl]-dimethylamine,
rac-trans-E-[4-benzylidene-2-(3-methoxy-phenyl)-cyclohexylmethyl]-dimethylamine,
rac-trans-Z-[4-benzylidene-2-(3-methoxy-phenyl)-cyclohexylmethyl]-dimethylamine,
rac-cis-Z-[4-benzylidene-2-(3-methoxy-phenyl)-cyclohexylmethyl]-dimethylamine,
rac-cis-E-3-[4-dimethylaminomethyl-3-(3-methoxy-phenyl)-cyclohexylidenemethyl]-benzoic acid methyl ester,
rac-cis-Z-3-[4-dimethylaminomethyl-3-(3-methoxy-phenyl)-cyclohexylidenemethyl]-benzoic acid methyl ester,
rac-trans-Z-3-[4-dimethylaminomethyl-3-(3-methoxy-phenyl)-cyclohexylidenemethyl]-benzoic acid methyl ester,
rac-trans-E-3-[4-dimethylaminomethyl-3-(3-methoxy-phenyl)-cyclohexylidenemethyl]-benzoic acid methyl ester,
Z-3-[4-dimethylaminomethyl-3-(3-methoxy-phenyl)-2-methyl-cyclohex-2-enylidenemethyl]-benzoic acid methyl ester,
E-3-[4-dimethylaminomethyl-3-(3-methoxy-phenyl)-2-methyl-cyclohex-2-enylidenemethyl]-benzoic acid methyl ester,
Z-3-[4-dimethylaminomethyl-3-(3-methoxy-phenyl)-2-methyl-cyclohex-2-enylidenemethyl]-naphthalene-1-carboxylic acid ethyl ester,
E-3-[4-dimethylaminomethyl-3-(3-methoxy-phenyl)-2-methyl-cyclohex-2-enylidenemethyl]-naphthalene-1-carboxylic acid ethyl ester,
Z-3-[4-dimethylaminomethyl-3-(3-methoxy-phenyl)-cyclohexylidenemethyl]-2-fluoro-benzoic acid ethyl ester,
Z-3-[4-dimethylaminomethyl-3-(3-methoxy-phenyl)-cyclohex-2-enylidenemethyl]-benzoic acid,
E-3-[4-dimethylaminomethyl-3-(3-methoxy-Phenyl)-cyclohex-2-enylidenemethyl]-benzoic acid,
E-{3-[4-dimethylaminomethyl-3-(3-methoxy-phenyl)-cyclohex-2-enylidenemethyl]-phenyl}-methanol,
rac-trans-Z-3-[4-dimethylaminomethyl-3-(3-methoxy-phenyl)-cyclohexylidenemethyl]-benzoic acid,
rac-trans-E-3-[4-dimethylaminomethyl-3-(3-methoxy-phenyl)-cyclohexylidenemethyl]-benzoic acid,
rac-trans-E-[3-(2-dimethylaminomethyl-5-(3-hydroxymethyl-benzylidene)-cyclohexyl)-phenol,
rac-trans-E-3-(5-benzylidene-2-dimethylaminomethyl-cyclohexyl)-phenol,
E-3-[4-dimethylaminomethyl-3-(3-methoxy-phenyl)-cyclohex-2-enylidenemethyl]-benzoic acid tert-butyl ester,
E-3-[2-dimethylaminomethyl-3-(3-hydroxymethyl-benzylidene)-cyclohex-1-enyl]-phenol,
rac-trans-Z-3-(5-benzylidene-2-dimethylaminomethyl-cyclohexyl)-phenol,
Z-3-[2-dimethylaminomethyl-5-(3-hydroxymethyl-benzylidene)-cyclohex-1-enyl]-phenol,
Z-{3-[4-dimethylaminomethyl-3-(3-methoxy-phenyl)-cyclohex-2-enylidenemethyl]-phenyl}-methanol,
rac-cis-E-4-dimethylaminomethyl-3-(3-methoxy-phenyl)-cyclohexylidenemethyl]-benzoic acid,
rac-cis-Z-3-[4-dimethylaminomethyl-3-(3-methoxy-phenyl)-cyclohexylidenemethyl]-benzoic acid,
rac-trans-E-3-[4-dimethylaminomethyl-3-(3-methoxy-phenyl)-cyclohexylidenemethyl]-benzoic acid tert-butyl ester,
rac-trans-E-{3-[4-dimethylaminomethyl-3-(3-methoxy-phenyl)-cyclohexylidenemethyl]-phenyl}-methanol,
rac-cis-Z-3-[4-dimethylaminomethyl-3-(3-methoxy-phenyl)-cyclohexylidenemethyl]-benzoic acid ethyl ester,
E-3-[4-dimethylaminomethyl-3-(3-methoxy-phenyl)-cyclohex-2-enylidenemethyl]-N,N-diethyl-benzamide,
rac-trans-E-3-[4-dimethylaminomethyl-3-(3-methoxy-phenyl)-cyclohex-2-enylidenemethyl]-N,N-diethyl-benzamide,
E-3-[4-dimethylaminomethyl-3-(3-methoxy-phenyl)-cyclohex-2-enylidenemethyl]-benzoic acid ethyl ester,
Z-3-[4-dimethylaminomethyl-3-(3-methoxy-phenyl)-cyclohex-2-enylidenemethyl]-N,N-diethyl-benzamide,
rac-cis-E-3-[4-dimethylaminomethyl-3-(3-methoxy-phenyl)-cyclohexylidenemethyl]-N, N-diethyl-benzamide,
rac-trans-Z-3-[4-dimethylaminomethyl-3-(3-methoxy-phenyl)-cyclohexylidenemethyl]-N,N-diethyl-benzamide,
E-3-[4-dimethylaminomethyl-3-(3-hydroxy-phenyl)-cyclohex-2-enylidenemethyl]-benzoic acid methyl ester,
Z-3-[4-dimethylaminomethyl 3-(3-hydroxy-phenyl)-cyclohex-2-enylidenemethyl]-benzoic acid methyl ester, Z-3-[4-dimethylaminomethyl 3-(3-methoxy-Phenyl)-cyclohex-2-enylidenemethyl]-benzoic acid isobutyl ester,
Z-3-[6-dimethylaminomethyl-3-(3-hydroxymethyl-benzylidene)-cyclohex-1-enyl]-phenol,
Z-[4-(4-chloro-benzylidene)-2-(3-methoxy-phenyl)-cyclohex-2-enylmethyl]-dimethyl-amino,
E-[4-(4-fluoro-benzylidene)-2-(3-methoxy-phenyl)-cyclohex-2-enYlmethyl]-dimethyl-amino,
Z-[4-(4-fluoro-benzylidene)-2-(3-methoxy-Phenyl)-cyclohex-2-enylmethyl]-dimethyl-amino,
E-3-[6-dimethylaminomethyl-3(4-fluoro-benzylidene)-cyclohex-1-enyl]-phenol,
Z-3-[6-dimethylaminomethyl-3-(4-fluoro-benzylidene)-cyclohex-1-enyl]-phenol,
E-[4-(4-chloro-benzylidene)-2-(3-methoxy-phenyl)-cyclohex-2-enylmethyl]-dimethyl-amine,
E-3-[3-(4-chloro-benzylidene) ±6-dimethylaminomethyl-cyclohex-1-enyl]-phenol,
Z-3-[4-dimethylaminomethyl-3-(3-hydroxy-phenyl)-cyclohex-2-enylidenemethyl]-benzoic acid methyl ester,
E-3-[4-dimethylaminomethyl-3-(3-hydroxy-phenyl)-cyclohex-2-enylidenemethyl]-benzoic acid,
rac-cis-E-3-[4-dimethylaminomethyl-3-(3-hydroxy-phenyl)-cyclohexylidenemethyl]-benzoic acid methyl ester,
rac-cis-Z-3-[4-dimethylaminomethyl-3-(3-hydroxy-phenyl)-cyclohexylidenemethyl]-benzoic acid methyl ester,
rac-trans-Z-3-[4-dimethylaminomethyl-3-(3-hydroxy-phenyl)-cyclohexylidenemethyl]-benzoic acid,
rac-trans-E-3-[4-dimethylaminomethyl-3-(3-hydroxy-phenyl)-cyclohexylidenemethyl]-benzoic acid,
rac-cis-Z-3-[4-dimethylaminomethyl-3-(3-hydroxy-phenyl)-cyclohexylidenemethyl]-benzoic acid,
rac-cis-Z-3-[4-dimethylaminomethyl-3-hydroxy-3-(3-methoxy-phenyl)-cyclohexylidenemethyl]-benzoic acid methyl ester,
rac-cis-E-3-[3-chloro-4-dimethylaminomethyl-3-(3-methoxy-phenyl)-cyclohexylidenemethyl]-benzoic acid methyl ester,
rac-cis-E-3-[4-dimethylaminomethyl-3-hydroxy-3-(3-methoxy-phenyl)-cyclohexylidenemethyl]-benzoic acid methyl ester,
rac-cis-Z-3-[4-dimethylaminomethyl-3-hydroxy-3-(3-methoxy-phenyl)-cyclohexylidenemethyl]-benzoic acid methyl ester,
(+)-trans-E-3-[4-dimethylaminomethyl-3-(3-methoxy-phenyl)-cyclohexylidenemethyl]-benzoic acid,
(−)-trans-B-3-[4-dimethylaminomethyl-3-(3-methoxy-phenyl)-cyclohexylidenemethyl]-benzoic acid,
rac-trans-E-3-(4-dimethylaminomethyl-3-phenyl-cyclohexylidenemethyl)-benzoic acid methyl ester,
rac-trans-Z-3-(4-dimethylaminomethyl-3-phenyl-cyclohexylidenemethyl)-benzoic acid methyl ester,
rac-cis-E-3-(4-dimethylaminomethyl-3-phenyl-cyclohexylidenemethyl)-benzoic acid,
rac-cis-E-3-(4-dimethylaminomethyl-3-phenyl-cyclohexylidenemethyl)-benzoic acid,
rac-trans-Z-3-(4-dimethylaminomethyl-3-phenyl-cyclohexylidenemethyl)benzoic acid,
rac-trans-E-3-(4-dimethylaminomethyl-3-phenyl-cyclohexylidenemethyl)-benzoic acid,
rac-trans-E-3-[4-dimethylaminomethyl-3-(3-trifluoromethyl-phenyl)-cyclohexylidenemethyl]-benzoic acid,
rac-trans-Z-3-[4-dimethylaminomethyl-3-(3-trifluoromethyl-phenyl)-cyclohexylidenemethyl]-benzoic acid,
rac-trans-E-3-[4-dimethylaminomethyl-3-(3-fluoro-phenyl)-cyclohexylidenemethyl]-benzoic acid methyl ester,
rac-trans-Z-3-[4-dimethylaminomethyl-3-(3-fluoro-phenyl)-cyclohexylidenemethyl] benzoic acid methyl ester,
rac-cis-E-3-[4-dimethylaminomethyl-3-(3-fluoro-phenyl)-cyclohexylidenemethyl]-benzoic acid methyl ester,
rac-trans-E-3-[4-dimethylaminomethyl-3-(3-fluoro-phenyl)-cyclohexylidenemethyl]-benzoic acid,
rac-trans-Z-3-[4-dimethylaminomethyl-3-(3-fluoro-phenyl)-cyclohexylidenemethyl]-benzoic acid,
rac-cis-E-3-[4-dimethylaminomethyl-3-(3-fluoro-phenyl)-cyclohexylidenemethyl]-benzoic acid,
E-[4-ethylidene-2-(3-methoxy-phenyl)-cyclohex-2-enylmethyl]-dimethylamine [4-isopropylidene-2-(3-methoxy-phenyl)-cyclohex-2-enylmethyl]-dimethylamine,
E-[2-(3-methoxy-phenyl)-4-propylidene-cyclohex-2-enylmethyl]-dimethylamine, and E-[4-butylidene-2-(3-methoxy-phenyl)-cyclohex-2-enylmethyl]-dimethylamineas.

59. A method for the treatment of pain, the method comprising administering to a patient in need thereof an effective amount of a pharmaceutical composition of claim 56.

60. A method for the treatment of urinary incontinence or diarrhea, the method comprising administering to a patient in need thereof an effective amount of a pharmaceutical composition of claim 56.

61. A method for the treatment of depression, drug or alcohol abuse, or coughing, the method comprising administering to a patient in need thereof an effective amount of a pharmaceutical composition of claim 56.

* * * * *